United States Patent
Chen

(10) Patent No.: US 8,470,873 B2
(45) Date of Patent: Jun. 25, 2013

(54) VITAMIN E SUCCINATE STABILIZED PHARMACEUTICAL COMPOSITIONS, METHODS FOR THE PREPARATION AND THE USE THEREOF

(75) Inventor: Andrew Xian Chen, San Diego, CA (US)

(73) Assignee: Mast Therapeutics, Inc., San Diego, CA (US)

( * ) Notice: Subject to any disclaimer, the term of this patent is extended or adjusted under 35 U.S.C. 154(b) by 211 days.

(21) Appl. No.: 11/702,014

(22) Filed: Feb. 1, 2007

(65) Prior Publication Data

US 2007/0207173 A1 Sep. 6, 2007

Related U.S. Application Data

(60) Provisional application No. 60/764,061, filed on Feb. 1, 2006, provisional application No. 60/771,816, filed on Feb. 8, 2006.

(51) Int. Cl.
*A61K 31/337* (2006.01)
*A61K 31/355* (2006.01)

(52) U.S. Cl.
USPC .......................... 514/449; 514/458; 424/450

(58) Field of Classification Search
None
See application file for complete search history.

(56) References Cited

U.S. PATENT DOCUMENTS

| | | | |
|---|---|---|---|
| RE32,393 E | 4/1987 | Wretlind et al. | |
| 4,816,247 A | 3/1989 | Desai et al. | |
| 5,415,869 A | 5/1995 | Straubinger et al. | |
| 5,439,686 A | 8/1995 | Desai et al. | |
| 5,478,860 A | 12/1995 | Wheeler et al. | |
| 5,616,330 A | 4/1997 | Kaufman et al. | |
| 5,621,001 A | 4/1997 | Canetta et al. | |
| 5,635,491 A | 6/1997 | Seki et al. | |
| 5,641,803 A | 6/1997 | Carretta et al. | |
| 5,665,761 A | 9/1997 | Canetta et al. | |
| 5,670,536 A | 9/1997 | Durr et al. ...................... 514/449 |
| 5,670,537 A | 9/1997 | Canetta et al. | |
| 5,714,520 A | 2/1998 | Jones et al. | |
| 5,750,142 A | 5/1998 | Friedman et al. | |
| 5,919,815 A | 7/1999 | Bradley et al. | |
| 5,977,172 A | 11/1999 | Yoshikawa et al. | |
| 6,028,108 A | 2/2000 | George | |
| 6,136,846 A | 10/2000 | Rubinfeld et al. ............ 514/449 |
| 6,140,373 A | 10/2000 | May et al. | |
| 6,231,600 B1 | 5/2001 | Zhong | |
| 6,245,349 B1 | 6/2001 | Yiv et al. | |
| 6,348,491 B1 | 2/2002 | Chu et al. | |
| 6,414,014 B1 | 7/2002 | Canetta et al. | |
| 6,455,280 B1 | 9/2002 | Edwards et al. | |
| 6,458,373 B1 * | 10/2002 | Lambert et al. ............... 424/405 |
| 6,469,069 B1 | 10/2002 | Mirejovsky et al. | |
| 6,660,286 B1 | 12/2003 | Lambert et al. ............... 424/405 |
| 6,793,938 B2 * | 9/2004 | Sankaram ...................... 424/489 |
| 6,858,227 B1 * | 2/2005 | Lal et al. ....................... 424/450 |
| 6,906,101 B1 * | 6/2005 | Bombardelli et al. ........ 514/463 |
| 6,979,456 B1 | 12/2005 | Parikh et al. .................. 424/422 |
| 7,030,155 B2 * | 4/2006 | Lambert et al. ............... 514/449 |
| 7,223,770 B2 * | 5/2007 | Zhang et al. .................. 514/283 |
| 7,786,164 B2 * | 8/2010 | Zhang et al. .................. 514/449 |
| 2002/0006613 A1 | 1/2002 | Shyjan et al. | |
| 2003/0065024 A1 | 4/2003 | Lambert et al. ............... 514/449 |
| 2003/0099674 A1 | 5/2003 | Chen .............................. 424/400 |
| 2005/0004002 A1 * | 1/2005 | Desai et al. ........................ 514/2 |
| 2005/0077497 A1 * | 4/2005 | Anderson ................... 252/299.1 |
| 2006/0008480 A1 | 1/2006 | Chen .............................. 424/400 |
| 2006/0024360 A1 | 2/2006 | Chen .............................. 424/450 |
| 2006/0067952 A1 | 3/2006 | Chen .............................. 424/400 |

FOREIGN PATENT DOCUMENTS

| | | | |
|---|---|---|---|
| EP | 1 510 206 A1 | | 3/2005 |
| WO | WO 99/04787 A1 | | 2/1999 |
| WO | WO 00/40236 A1 | | 7/2000 |
| WO | WO 03/074027 | * | 9/2003 |
| WO | WO 2005/065676 A1 | | 7/2005 |
| WO | WO 2005/065677 A1 | | 7/2005 |
| WO | WO 2006/015120 A2 | | 2/2006 |

* cited by examiner

*Primary Examiner* — Agnieszka Boesen
(74) *Attorney, Agent, or Firm* — Kilpatrick Townsend & Stockton LLP

(57) ABSTRACT

The present invention provides vitamin E succinate (VES)-stabilized compositions, methods for the preparation thereof and methods useful for the in vivo delivery of substantially water insoluble and optionally chemically unstable pharmacologically active agents (such as docetaxel).

27 Claims, No Drawings

VITAMIN E SUCCINATE STABILIZED PHARMACEUTICAL COMPOSITIONS, METHODS FOR THE PREPARATION AND THE USE THEREOF

CROSS-REFERENCE TO RELATED APPLICATIONS

This application claims the benefit of U.S. Provisional Patent Application Nos. 60/764,061 (filed Feb. 1, 2006) and 60/771,816 (filed Feb. 8, 2006).

BACKGROUND OF THE INVENTION

1. Field of the Invention

The present invention relates to an emulsion composition for the intravenous administration of pharmacologically active agents, as well as methods for preparation thereof.

2. Description of the Related Art

Docetaxel is an antineoplastic agent belonging to the taxoid family. The chemical name for docetaxel is (2R,3S)-N-carboxy-3-phenylisoserine,N-tert-butyl ester, 13-ester with 5β-20-epoxy-1,2α-,4,7β,10β,13α-hexahydroxytax-11-en-9-one 4-acetate 2-benzoate, trihydrate. Docetaxel has the following structural formula:

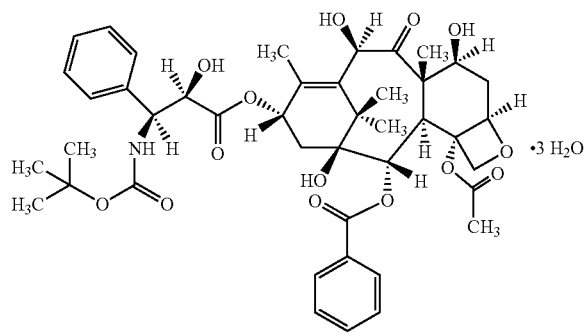

Docetaxel is highly lipophilic and practically insoluble in water. Because of the ester group (N-tert-butyl ester), docetaxel is very unstable in the presence of water as hydrolysis of the N-tert-butyl ester can take place rapidly.

In order to inject docetaxel intravenously, the marketed product (TAXOTERE™) is provided as a yellow viscous liquid containing docetaxel dissolved in almost 100% polysorbate 80, which is used as solubilizer for docetaxel. Polysorbate 80, like other detergents, is, however, very toxic. Upon intravenous injection, it causes severe allergic or hypersensitivity reactions that can be fatal. For this reason, the FDA has requested the drug maker to place a the following strong warning ("black box" warning) on the TAXOTERE™ label:

"Severe hypersensitivity reactions characterized by generalized rash/erythema, hypotension and/or bronchospasm, or very rarely fatal anaphylaxis, have been reported in patients who received the recommended 3-day dexamethasone premedication. Hypersensitivity reactions require immediate discontinuation of the TAXOTERE infusion and administration of appropriate therapy. TAXOTERE must not be given to patients who have a history of severe hypersensitivity reactions to TAXOTERE or to other drugs formulated with polysorbate 80."

Many efforts have been made to provide safer formulations for insoluble intravenous (IV) drugs such as docetaxel. The best-known example is another insoluble taxoid analog drug paclitaxel, which in its marketed product (TAXOL®) utilizes another immunogenic detergent called cremophor. Some improvements in solubilization methods have been reported for paclitaxel. These new formulations of paclitaxel represent improvements over the TAXOL® formulation. However, when it comes to the docetaxel formulation, virtually all previously reported solubilization methods for paclitaxel or docetaxel appear to suffer one or more of the following drawbacks:

(1) They contain toxic, allergenic or vein irritating excipients including solvents (e.g., ethanol, DMA, DMSO, propylene glycol, and n-methylpyrrolidon), solubilizers (e.g., polysorbates, cremophor, and bile salts), materials derived from an animal source with risk of virus contamination (e.g., human albumin) or chemicals that have no proven record of safe use (e.g., vitamin E TPGS).

(2) They contain water. As indicated above, docetaxel is incompatible with water.

(3) They are unstable and unable to deliver the required dose of docetaxel without a large and pharmaceutically unsafe amount of excipients such as phospholipids (as in liposome) or oil (previously known emulsions).

Accordingly, there is a need for developing a safe and stable formulation to deliver docetaxel and other water insoluble drugs. The present invention meets this need and provides additional related advantages.

BRIEF SUMMARY OF THE INVENTION

The present invention provides compositions for delivering substantially water insoluble pharmacologically active agents, methods for making and methods for using such compositions.

In one aspect, the present invention provides an oil-in-water emulsion comprising oil droplets in an aqueous medium, wherein the oil droplets comprise a substantial portion of a substantially water insoluble pharmacologically active agent, the average diameter of the droplets is no greater than about 1 micron, the emulsion is stabilized by vitamin E succinate (VES, or another alpha tocopheryl succinate or its analogues or salts thereof), and the emulsion has a zeta potential between −20 mV and −50 mV.

In certain embodiments, the oil droplets comprise no less than about 70%, 75%, 80%, 85%, 90%, 95%, or 98% of the substantially water insoluble pharmacological active agent. In certain embodiments, the average diameter of the droplets is no greater than about 500 nm, 400 nm, 300 nm, 200 nm, 150 nm, or 100 nm. In certain embodiments, the substantially water insoluble pharmacological active agent is a taxoid drug (e.g., docetaxel and paclitaxel). In certain embodiments, the taxoid drug is paclitaxel or docetaxel. In certain embodiments, the emulsion has a zeta potential between −20 mV and −50 mV. In certain embodiments, the emulsion has a zeta potential between −35 mV and −45 mV. In certain embodiments, the emulsion is sterilized by filtration. In certain embodiments, the oil phase of the emulsion is a liquid or is free of crystalline solid at ambient temperature, and the pharmacologically active agent is substantially dissolved in the oil phase.

In certain embodiments, the emulsion is prepared by a double-homogenization technique comprising: homogenizing VES in water to form a submicron VES suspension, dissolving a substantially water insoluble pharmacologically active agent in an oil solution containing at least one injectable oil and at least one injectable phospholipid to form an oil phase, combining the VES suspension, the oil phase and optionally other pharmaceutically acceptable ingredients, and homogenizing the mixture to produce a VES-stabilized emulsion.

In certain embodiments, the pharmacologically active agent is a water insoluble drug selected from the group consisting of an antineoplastic, antibiotic, antifungal, antiviral, antiinfective, antiinflammatory, antacid, antiadrenergic, anticholinergic, antiaggregatory, antialcoholic, antiallergic, analgestic, antiarryhthmia, antimycotic, antipsychotic, antipruritic, antidepressant, antihypertensive, anesthetic agent, antidiabetic, anti-hormone, hormones, drugs for lipid disorders, drugs for immune system disorders, drugs for metabolism disorders and drugs for hematological disorders.

In another aspect, the present invention provides a solid composition containing a substantially water insoluble pharmacologically active agent and is substantially free of water. The solid composition is prepared by removal of water from the composition described above, and can be rehydrated with water to form an emulsion suitable of injection. The average diameter of the re-formed emulsion droplets is no greater than about 1 micron. In certain embodiments, the average diameter of the re-formed emulsion droplets is no greater than about 500 nm, 400 nm, 300 nm, 200 nm, or 150 nm.

In another embodiments, the present invention provides an oil-in-water emulsion that comprises docetaxel or paclitaxel, VES, at least one injectable oil, injectable phospholipids and water, wherein the emulsion has a zeta potential between −20 mV and −50 mV, the average diameter of the said emulsion droplet is less than 200 nm, and the docetaxel- or paclitaxel-to-oil ratio is no less than 1:50 by weight.

In certain embodiments, the emulsion comprises docetaxel or paclitaxel in a weight percentage concentration range of 0.1 to 1, vitamin E succinate in a weight percentage concentration range of 0.01 to 5, a vegetable oil in a weight percentage concentration range of 1 to 10, optionally, a medium chain triglyceride oil in a weight percentage concentration range of 1 to 10, a phospholipid in a weight percentage concentration range of 1 to 20, optionally, cholesterol in a weight percentage concentration range of 0.01 to 5, and water in a weight percentage concentration range of 40 to 90. In addition, the pH of the emulsion is about 5 to 9. In certain embodiments, the emulsion further comprises a bulking agent selected from dextrose, sucrose, lactose and a mixture thereof in a weight percentage concentration range of 5 to 50.

In another aspect, the present invention provides a solid composition that comprises docetaxel or paclitaxel, is substantially free of water, and is prepared by removal of water from the emulsion as described above. The solid composition can be rehydrated with water to form an emulsion suitable of injection, and the average diameter of the re-formed emulsion droplets is no greater than about 1 micron. In certain embodiments, the average diameter of the re-formed emulsion droplets is no greater than about 500 nm, 400 nm, 300 nm, 200 nm, or 150 nm.

In certain embodiments, the solid composition comprises docetaxel or paclitaxel in a weight percentage concentration range of 0.2 to 3, vitamin E succinate in a weight percentage concentration range of 0.1 to 12, a vegetable oil in a weight percentage concentration range of 1.1 to 21.9, optionally, a medium chain triglyceride oil in a weight percentage concentration range of 1.1 to 21.9, a phospholipid in a weight percentage concentration range of 2.7 to 54.8, optionally, cholesterol in a weight percentage concentration range of 0.2 to 3.3, and a bulking agent selected from dextrose, sucrose, lactose, and a mixture thereof in a weight percentage concentration range of 4.7 to 93.2.

In another aspect, the present invention provides a method of treating a susceptible neoplasm comprising administering a pharmaceutically effective amount of an emulsion or a solid composition that comprises an anti-cancer drug as described above to a mammal in need thereof. In certain embodiments, the mammal is a human. In certain embodiments, the administration is by an injection route selected from the group consisting of intravenous, intraabdominal, intraarterial, intraarticular, intracapsular, intracervical, intracranial, intraductal, intradural, intralesional, intralocular, intralumbar, intramural, intraocular, intraoperative, intraparietal, intraperitoneal, intrapleural, intrapulmonary, intraspinal, intrathoracic, intratracheal, intratympanic, intrauterine, and intraventricular administration, by oral administration, and by instillation in a form of ophthalmic drops.

In another aspect, the present invention provides a double-homogenization technique for preparing a VES stabilized emulsion for delivering a substantially water insoluble pharmacologically active agent, comprising: homogenizing VES in water to form a submicron VES suspension, dissolving the substantially water insoluble pharmacologically active agent in an oil solution containing at least one injectable oil and at least one injectable phospholipid to form an oil phase, combining the VES suspension, the oil phase and optionally other pharmaceutically acceptable ingredients, and homogenizing the mixture to produce the emulsion.

In one aspect, the present invention provides a suspension comprising submicron solid particles of an amorphous or crystalline pharmacologically active agent dispersed in an aqueous medium and stabilized by VES, wherein the solid particles are substantially free of liquid oil, have an average diameter of less than 200 nm and a zeta potential between −20 mV and −50 mV.

In certain embodiments, the pharmacologically active agent is docetaxel or paclitaxel, and the suspension comprises docetaxel or paclitaxel in a weight percentage concentration range of about 0.1 to about 1.0, lecithin in a weight percentage concentration range of about 5 to about 15, cholesterol in a weight percentage concentration range of about 0.5 to about 2, VES in a weight percentage concentration range of about 0.1 to about 5, a bulking agent selected from sucrose, dextrose, lactose, and a mixture thereof in a weight percentage concentration range of about 10 to about 20, and water.

In one aspect, the present invention provides a solid composition comprising docetaxel in a weight percentage concentration range of about 1.3 to about 2.0, vitamin E succinate in a weight percentage concentration range of about 1 to about 15, a phospholipid selected from soy lecithin and egg lecithin in a weight percentage concentration range of about 22 to about 32, cholesterol in a weight percentage concentration range of about 1 to about 5, and a bulking agent selected from dextrose, sucrose, lactose, and a mixture thereof in a weight percentage concentration range of about 35 to about 75.

In another aspect, the present invention provides a method for preparing a suspension that comprises a pharmacologically active agent, comprising: (1) homogenizing an aqueous suspension of VES to form a submicron suspension of VES, (2) dissolving a pharmacologically active agent, phospholipids and cholesterol in ethanol and subsequently removing the ethanol to produce a solid mass, (3) combining the VES suspension and the solid mass, water and optionally a bulking agent to form a crude suspension, and (4) homogenizing the crude suspension to form a submicron suspension. In certain embodiments, the method further comprises the step of sterilizing the submicron suspension (e.g., via filtration).

DETAILED DESCRIPTION OF THE INVENTION

The current invention provides compositions, methods for the preparation thereof and methods useful for the in vivo delivery of substantially water insoluble and optionally chemically unstable pharmacologically active agents (such as docetaxel) in which the pharmacologically active agent is delivered in the form of an emulsion stabilized by vitamin E succinate (VES) (or its analogues or salts). In particular, an oil-in-water emulsion composition comprising the highly insoluble and unstable docetaxel dissolved in oil droplets having a submicron diameter and a zeta potential between −20 mV and −50 mV is provided. The VES-stabilized emulsion is capable of delivering a taxoid drug at an unusually high drug-to-oil ratio (e.g., 1:50 by weight), having small droplets (e.g., <200 nm), and providing a superior stability such that the emulsion can be dried by various drying methods to become devoid of its water and to form a solid composition. The removal of water stabilizes docetaxel or other chemically unstable pharmacologically active agents resulting from hydrolysis. The solid composition can be rehydrated with water to form an oil-in-water emulsion comprising droplets of a diameter of less than about 1 micron and a negative zeta potential value. This invention also relates to a "double-homogenization technique" useful for the preparation of the VES-stabilized emulsion. This technique can reliably produce emulsions that are of small droplet size, can be easily filtered to sterilize, and require a short drying time. The VES-stabilized emulsion of docetaxel described in this invention corrects several clinically important deficiencies in the current marketed formulations and yields favorable safety and efficacy profiles when compared to the marketed product TAXOTERE™.

VES is not a typical surfactant: It is not soluble in oil (i.e., not lipophilic) or in water (i.e., not hydrophilic either). Surfactants are generally characterized by an HLB value (hydrophilic-lipophilic balance). A surfactant with a high HLB (>7) is water-soluble and with low HLB (<7) is oil soluble. VES dose not naturally disperse well in water at neutral pH (pH 5-8), e.g., it behaves like a wax in water unless a high-pressure homogenization is applied to form a submicron suspension. VES is therefore regarded as a unique "amphiphobic" molecule, which is different from other emulsion emulsifiers or stabilizers reported previously such as oleic acid, polysorbate 80, vitamin E TPGS, phospholipids, etc., in that the previously known emulsion emulsifiers are either water soluble (polysorbate 80, vitamin E TPGS) or oil soluble (oleic acid, phospholipid).

Not wishing to be bound by a theory, the present invention takes the somewhat unorthodox approach to taking advantage of the amphiphobic nature of VES to stabilize the oil droplets by impacting negative charges on the droplet surface. It is speculated by the inventor that the submicron sized particles of VES (obtained after the first high-pressure homogenization) remain preferentially in the interfacial area between the oil droplets and the surrounding aqueous solution, effectively coat the droplets with a negative charge and thus prevent the droplets from adhering to each other by the repulsive electrostatic forces.

The composition provided by the present invention is different from those previously disclosed. For example, Lambert et al. (U.S. Pat. No. 6,660,286) disclosed an emulsion composition for paclitaxel—which is insoluble but very stable in the presence of water given the lack of hydrolysable ester groups in this particular taxoid. The emulsion composition comprises vitamin E as the primary oil phase component, a PEGylated vitamin E or vitamin E TPGS as the emulsifier and water in the aqueous phase. This composition is not applicable to docetaxel because of the presence of water and the hydrolysable ester group present in docetaxel. Furthermore, vitamin E TPGS has not been used in any approved intravenous drug product at the time of this application, and therefore its safety is uncertain.

In addition, the emulsion disclosed in the present invention is stabilized by VES and is made to have a zeta potential in a desired range for an improved stability and safety. Physically, VES differs greatly from vitamin E or vitamin E TPGS in terms of solubility, whereby, vitamin E is soluble in oil, and vitamin E TPGS is soluble in either oil or water, whereas VES is insoluble in either oil or water, i.e., cannot be used as an oil phase, thus its function as a stabilizer in the VES-stabilized emulsion is unique and different from the other vitamin E derivative used in composition according to U.S. Pat. No. 6,660,286. The double-homogenization technique according to the present invention was developed to incorporate VES into an emulsion because of its lack of solubility in either water or oil.

The compositions provided by the present invention are also different from those disclosed in Koichi et al. (PCT Application Publication Nos. WO 2005065677 and WO 2005065676). Those PCT application publications disclosed a fat emulsion for use in solubilizing at least one active ingredient selected from the group consisting of paclitaxel and docetaxel. This fat emulsion contained an oily ingredient, an emulsifying agent, and a stabilizer, e.g., phosphatidylglycerol and fatty acids. The fat emulsions as disclosed by Koichi et al. are aqueous emulsions and are not suitable for drying due to absence of a bulking agent. Drying such emulsion composition would result in extensive aggregation of the droplets and destruction of the emulsion by phase separation, which is unacceptable for intravenous injection. Therefore, the previously disclosed composition is meant to remain in an oil-in-water liquid emulsion and thus is not a feasible composition for docetaxel, which undergoes a rapid degradation by hydrolysis in presence of water. The VES-stabilized emulsion of this invention can be dried by various drying method including vacuum-dry, spray-dry and freeze-dry to render a solid composition that is substantially free of water and can be reconstituted with water to form an emulsion with droplet size remaining below 1 micron and suitable for intravenous injection.

The compositions provided by the present invention are also different from those disclosed by Parikh et al. (U.S. Pat. No. 6,979,456). That U.S. patent describes pharmaceutical dosage forms for anticancer drugs, and paclitaxel in particular; the active drug is formulated as a storage stable self-emulsifying pre-concentrate. A self-emulsifying pre-concentrate is a non-aqueous composition that upon mixing with water forms an emulsion. This absence of water in the pre-concentrate formulation is a desirable feature for docetaxel, however, the pre-concentrate compositions disclosed have numerous ingredients that are not safe to inject, e.g., 20-80% non-ionic surfactants, up to 35% w/w diethylene glycol monoethylether, and up to 40% w/w of a hydrophilic component selected from the group consisting of a hydroxyalkane, a dihydroxyalkane, a polyethylene glycol having an average molecular weight of about 1000, and combinations thereof. These pre-concentrate compositions, as claimed by the inventors, are indeed for oral administration and not for injection.

The compositions provided by the present invention are also different from the formulation disclosed in a previous application (Chen, U.S. Patent Application Publication No. 20030099674). In that application, this inventor disclosed a lyophilized formulation containing a taxoid drug, a lecithin, a medium chain triglyceride, and anti-adhesion agent comprising a saccharide with a collapse temperature in a range of −25 degree C. to about −30 degree C., with the same purposes, i.e., to provide a non-toxic and stable emulsion formulation for a taxoid drug like paclitaxel or docetaxel. The invention disclosed in this application represents a significant improvement over the previous application in the following important aspects: (1) increased drug-to-oil ratio; (2) reduced droplet size; (3) increased stability; (4) shortened emulsion preparation process time; and (5) improved safety. All these improvements may be accomplished by the use of VES as the stabilizer in the composition. It was discovered by this inventor that VES, even used at a very low concentration such as 0.1-0.5% in the emulsion composition, can have a profound impact on emulsion stability, droplet size, drug loading, emulsion preparation process time, and safety.

For example, the present invention greatly reduces oil concentration required to dissolve the given amount of a taxoid drug, i.e., drug-to-oil ratio in the emulsion composition. The emulsion composition disclosed in the previous application has a drug-to-oil ratio of about 1 to 150-187 by weight, i.e., it takes 150 to 187 weight parts of oil to dissolve one part of a drug such as paclitaxel (Example 5, U.S. Patent Application Publication No. 20030099674) whereas a VES-stabilized emulsion can achieve a drug-to-oil ratio as low as 1 to 13 by weight. A lower oil-to-drug ratio is desired for a reduced risk of hyperlipidemia, improved emulsion stability, and greatly shortened freeze-drying time. In addition, the average droplet size in a previously disclosed formulation is about 200-210 nm (Example 5, U.S. Patent Application Publication No. 20030099674), which is merely filterable through a 0.2 micron sterilizing filter, whereas the VES-stabilized emulsion of this invention has a droplet size of about 105 to 150 nm. An emulsion with a smaller droplet size is preferred as the small droplets can facilitate transport of the drug in the blood circulation, reduce risk of pulmonary embolism (clog the capillary blood vessel in lung), and allow for a much easier manufacturing process with regard to ease of filtration to achieve sterilization. Again, the reduced droplet size is made possible by use of VES as the stabilizer and the double-homogenization technique.

The nature of the VES-stabilized emulsion differs from the emulsion disclosed in U.S. Patent Application Publication No. 20030099674, whereby the zeta potential of the droplets is between −20 mV and −50 mV for the VES-stabilized emulsion and between 0 and −10 mV for the emulsion of the previous application. Zeta potential is a measure of the magnitude of the repulsion or attraction between particles/droplets. It is discovered by this inventor that zeta potentials between −20 mV and −50 mV are highly desirable for an improved emulsion stability and safety. This inventor observed that emulsion compositions with no or insufficient level of VES have a zeta potential between 0 to −20 mV and are less stable compared to emulsions with zeta potential between −20 mV and −50 mV. This inventor also discovered that an excessively highly negative zeta potential (−60 mV to −70 mV) results in the emulsion being more toxic in animal model, possibly by directing the cytotoxic docetaxel to the liver. Therefore, it is of important for an emulsion composition, especially one that carries a potent or cytotoxic pharmacologically active agent such as a docetaxel, to possess a zeta potential in the desired range where the emulsion is both stable and safe. Emulsion compositions disclosed in this invention differentiate from other previously disclosed emulsions by having a zeta potential in the most desirable range of about −20 mV to −50 mV.

A. VES-Stabilized Compositions for Delivering Substantially Water Insoluble Agents In one aspect, the present invention provides VES-stabilized compositions for delivering substantially water insoluble pharmacologically active agents. Such compositions may be oil-in-water emulsions, solid compositions that may be re-constituted to oil-in-water emulsions, and colloidal dispersions, which all comprise a sufficient amount of VES for their stability.

Vitamin E succinate or "VES" as referred to in this application is also chemically named as alpha-tocopheryl succinate. The terms of VES and alpha-tocopheryl succinate are used interchangeably in this application.

Alpha tocopherol is (±)-(2RS,4'RS,8'RS)-2,5,7,8-tetramethyl-2-(4',8',12'-trimethyltridecyl)-6-chromanol. Its non-proprietary names include Alpha Tocopherol by British Pharmacopoeia, α-Tocopherolum by PhEur, and Vitamin E by the United State Pharmacopoeia. Its CAS Registry Number is 10191-41-0. Its empirical formula is $C_{29}H_{50}O_2$ and molecular weight is 430.69. The structures of alpha tocopherol and its homologues are shown below.

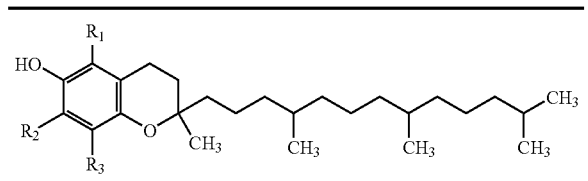

$R_1$, $R_2$, and $R_3$ may be H or $CH_3$.

| Homologues | R1 | R2 | R3 |
|---|---|---|---|
| Alpha-tocopherol | CH3 | CH3 | CH3 |
| Beta-tocopherol | CH3 | H | CH3 |
| Gamma-tocopherol | H | CH3 | CH3 |
| Delta-tocopherol | H | H | CH3 |

The naturally occurring form is known as d-alpha tocopherol or simply alpha tocopherol. Alpha tocopherol has three chiral centers giving rise to eight isomers. The d-isomeric form represents the (2R,4'R,8'R)-alpha-tocopherol or sometimes, RRR-alpha-tocopherol.

"Alpha-tocopheryl succinate" refers to a hemi-ester of succinic acid with alpha tocopherol, such as d-alpha-tocopheryl acid succinate ($C_{33}H_{54}O_5$, MW 530.8, CAS number 4345-03-3). The chemical structures of alpha-tocopheryl succinate and its analogues are shown below.

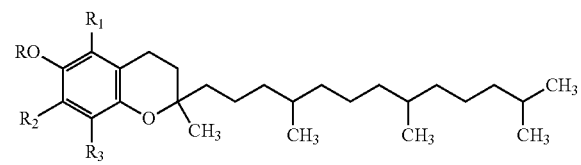

$R_1$, = $R_2$, = $R_3$ = H or $CH_3$ $R = -OOC-(CH_2)_n-COOH$

| Analogues | n | Dicarboxylic acids |
|---|---|---|
| Alpha-tocopheryl oxalate | 0 | Oxalic acid |
| Alpha-tocopheryl malonate | 1 | Malonic acid |
| Alpha-tocopheryl succinate | 2 | Succinic acid |
| Alpha-tocopheryl glutarate | 3 | Glutaric acid |
| Alpha-tocopheryl adipate | 4 | Adipic acid |
| Alpha-tocopheryl pimelate | 5 | Pimelic acid |
| Alpha-tocopheryl suberate | 6 | Suberic acid |
| Alpha-tocopheryl azelate | 7 | Azelaic acid |

VES or "alpha-tocopheryl succinate," in certain embodiments, may include isomers such as dl-alpha-tocopheryl acid succinate (CAS number 17407-37-3). It may, in certain embodiments, include beta tocopheryl acid succinate, delta tocopheryl acid succinate, gamma tocopheryl acid succinate, or isomers thereof.

In certain embodiments, the compositions for delivering substantially water insoluble pharmacological active agents may be stabilized by an analogue or salt of VES.

The term "alpha-tocopheryl succinate analogues" or "VES analogues" used in this invention refers to hemi-esters of short-chain dicarboxylic acids with alpha tocopherol, wherein the dicarboxylic acids have the general type formula:

$$\text{HOOC—(CH}_2)_n\text{—COOH}$$

Short-chain dicarboxylic acids include oxalic acid (n=0), malonic acid (n=1), succinic acid (n=2), glutaric acid (n=3), adipic acid (n=4), pimelic acid (n=5), suberic acid (n=6), and azelaic acid (n=7) acids.

The term "alpha-tocopheryl succinate salts" or "VES salts" used in this invention refers to an ionic ion salt of pharmaceutically acceptable inorganic counter ions (e.g., sodium, potassium, lithium, calcium, magnesium, and aluminum) and organic counter ions (e.g., amines, lysine, and arginine).

VES or alpha-tocopheryl succinate, a hemi-ester of alpha tocopherol, is structurally and functionally different from the other three common types of vitamin E derivatives: tocopherol, tocopherol monoester (e.g., acetate), and tocopherol polyetheleneglycol succinate (also referred to as tocopherol PEG ester or vitamin E TPGS). The hemi-esters contain an open (non-esterified) carboxylic acid group and are ionizable, whereas all the others are non-ionizable. Thus, when included as a component in a formulation, the hemi-esters function very different from the monoesters or the parent tocopherol. While a monoester or the parent tocopherol is lipophilic and oil soluble, the hemi-esters are not soluble in either water or oil and are not good solvent or solubilizer for either hydrophilic or hydrophobic drugs. When the open (non-esterified) carboxylic acid group on a hemiester is ionized at a pH about 7 or above, the hemi-esters behave like a surfactant of low HLB value (i.e. water insoluble type) and yet they are not good surfactants like vitamin E TPGS. For example, unlike vitamin E TPGS, tocopherol succinate is incapable of solubilizing a lipophilic drug by forming micelles in water, or emulsifying an vegetable oil in water to form a stable oil-in-water emulsion. By appearance, tocopherol succinate is a crystalline solid, whereas tocopherol and tocopherol acetate are oily liquid, and vitamin E TPGS is a water-soluble wax-like material.

In certain embodiments, the formulations of the present invention do not comprise alpha-tocopherol, vitamin E TPGS, or either of them.

A "VES-stabilized" composition refers to a composition that comprises a sufficient amount of VES (or its analogue or salt) so that the composition is chemically and/or physically stable.

A composition is "chemically stable" if the pharmacologically active agent (e.g., docetaxel) in the composition is not substantially chemically degraded after storage under appropriate conditions for at least one month. In certain embodiments, the concentration of the intact docetaxel in the composition is reduced by less than about 1%, 3%, 5% or 10% under appropriate storage conditions (e.g., at −20° C., 2-8° C., or room temperature) for at least 1, 2, 3, 4, 5, 6, 9, 12, 15, 18, or 24 months.

Chemical degradation of docetaxel (or its hydrates) includes mainly hydrolysis of the N-tert-butyl ester bond. The rate of hydrolysis of docetaxel is pH-dependent. The removal of water in the continuous phase by vacuum-drying, freeze-drying, spray-drying, or other drying means essentially stops the hydrolytic degradation.

A composition (e.g., a emulsion or a dried emulsion) is "physically stable" if it may be stored under appropriate conditions for at least 1 month without increase in its average particle size by more than 100%, or evidence of phase separation, creaming, or particle aggregation. In certain embodiments, the average size of particles of a composition of the present invention does not increase by more than about 10%, 20%, 25%, 30%, 40%, 50%, 75%, or 100% under appropriate storage conditions (e.g., at −20° C., 2-8° C., or room temperature) for at least 1, 2, 3, 4, 5, 6, 9, 12, 15, 18, or 24 months.

In certain embodiments, an emulsion composition of docetaxel is capable of retaining no less than 90% of the intact docetaxel (or its hydrate) and is substantially free from aggregates of greater than 5-micron in diameter for at least 6 months at room temperature. In certain embodiments, an emulsion composition of docetaxel is capable of retaining no less than 92%, 94%, 95%, 96%, 97%, 98% or 99% of the intact docetaxel (or its hydrate).

In certain embodiments, the concentration of VES (or its analogue or salt) in a VES-stabilized emulsion (prior to being dried) or a colloidal composition of the present invention is about 0.1% to about 2% by weight, such as about 0.1% to about 1.2% and about 0.2% to about 0.5% by weight. In certain embodiments, the concentration is about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% by weight.

"Pharmacologically active agent" refers to any compound natural or synthetic that has therapeutic effects on a mammal (including human). Therapeutic agents include anticancer agents (e.g., chemotherapeutic agents) and may be used alone or in addition to docetaxel in the same formulation.

The term "substantially water insoluble" refers to the lack of solubility of a pharmacologically active agent in aqueous solutions (such as water, physiological saline, injectable dextrose solutions, etc). The USP/NF generally expresses the solubility in terms of the volume of solvent required to dissolve 1 gram of the drug at a specified temperature (e.g., 1 g aspirin in 300 ml H$_2$O, 5 ml ethanol at 25° C.). Other references may use more subjective terms to describe solubility, such as those given in the following table from Remington's Pharmaceutical Sciences, Mack Publishing Co., Easton, Pa., latest edition.

| Descriptive terms | Parts of solvent needed for 1 part solute |
|---|---|
| Very soluble | <1 |
| Freely soluble | 1-10 |
| Soluble | 10-30 |
| Sparingly soluble | 30-100 |
| Slightly soluble | 100-1000 |
| Very slightly soluble | 1000-10,000 |
| Practically insoluble or insoluble | >10,000 |

Therefore, the "substantially water insoluble pharmacologically active agents" of this invention include the pharmacologically active agents in the bottom four solubility categories, i.e., "sparingly soluble," "slightly soluble," "very slightly soluble," and "practically insoluble or insoluble" when water is used as the solvent.

The term "insoluble" may be used interchangeably with hydrophobic, lipophilic, oleophilic, and similar terms.

"Chemotherapeutic agents" refer to any natural or synthetic molecules that are effective against one or more forms of cancer (e.g., breast, ovarian, and lung cancer). In certain embodiments, the chemotherapeutic agents are slightly or completely lipophilic, or can be modified to be lipophilic. Chemotherapeutic agents include molecules that are cytotoxic (anti-cancer agents), that stimulate the immune system (immune stimulators), and that modulate or inhibit angiogenesis.

Chemotherapeutics include, but are not limited to, alkylating agents, antimetabolites, taxanes, cytotoxics, cytoprotectant adjuvants, LHRH analogues, platinum agents, antiestrogens, anti-androgens, hormonals, aromatase inhibitors, cell cycle controlling agents, apoptosis agents, topoisomerase inhibitors, angiogenesis inhibitors, immunotherapy agents, monoclonal antibodies, retinoid, kinase inhibitors and signal transduction inhibitors.

In certain embodiments, the chemotherapeutic is selected from paclitaxel, docetaxel and related molecules collectively termed taxoids, taxines or taxanes.

In certain embodiments, the chemotherapeutic is selected from podophyllotoxins and their derivatives and analogues.

In certain embodiments, chemotherapeutics useful in this invention are camptothecins, and platins.

In certain other embodiments, chemotherapeutics useful in this invention are the lipophilic anthracyclines.

In certain other embodiments, chemotherapeutics useful in this invention are compounds that are lipophilic or can be made lipophilic by molecular chemosynthetic modifications well known to those skilled in the art, for example, by combinatorial chemistry and by molecular modeling. Such chemotherapeutics include: Amonafide, Illudin S, 6-hydroxymethylacylfulvene Bryostatin 1,26-succinylbryostatin 1, Palmitoyl Rhizoxin, DUP 941, Mitomycin B, Mitomycin C, Penclomedine, interferon alpha.2b, angiogenesis inhibitor compounds (e.g., cisplatin hydrophobic complexes such as 2-hydrazino-4,5-dihydro-1H-imidazole with platinum chloride and 5-hydrazino-3,4-dihydro-2H-pyrrole with platinum chloride), vitamin A and its derivatives.

Other chemotherapeutics useful in the invention include: 1,3-bis(2-chloroethyl)-1-nitrosurea ("carmustine" or "BCNU"), 5-fluorouracil, doxorubicin ("adriamycin"), epirubicin, aclarubicin, Bisantrene (bis(2-imidazolen-2-ylhydrazone)-9,10-anthracenedicarboxaldehyde, mitoxantrone, methotrexate, edatrexate, muramyl tripeptide, muramyl dipeptide, lipopolysaccharides, 9-b-d-arabinofairanosyladenine ("vidarabine") and its 2-fluoro derivative, gemcitabine, resveratrol, retinoic acid and retinol, carotenoids, and tamoxifen.

Other chemotherapeutics useful in this invention include: Decarbazine, Lonidamine, Piroxantrone, Anthrapyrazoles, Etoposide, Camptothecin, 9-aminocamptothecin, 9-nitrocamptothecin, camptothecin-11 ("Irinotecan"), Topotecan, Bleomycin, the Vinca alkaloids and their analogs [Vincristine, Vinorelbine, Vindesine, Vintripol, Vinxaltine, Ancitabine], 6-aminochrysene, 17-allylamino geldanamycin, combrestatin, camptothecin, thalidomide, and vinorelbine.

Other chemotherapeutics useful in the application of the invention are mimetics of taxol, eleutherobins, sarcodictyins, discodermolides and epothiolones.

In certain other embodiments, pharmacologically active agents used in this invention include water a insoluble drug selected from the group consisting of an antineoplastic, antibiotic, antifungal, antiviral, antiinfective, antiinflammatory, antiacid, antiadrenergic, anticholinergic, antiaggregatory, antialcoholic, antiallergic, analgestic, antiarryhthmia, antimycotic, antipsychotic, antipruritic, antidepressant, antihypertensive, anesthetic agent, antidiabetic, anti-hormone, hormone, drug for lipid disorders, drug for immune system disorders, drug for metabolism disorders and drug for hemological disorders.

Substantially water insoluble pharmacologically active agents contemplated for use in the practice of the present invention include pharmaceutically active agents, diagnostic agents, agents of nutritional value, and the like. Examples of pharmaceutically active agents include: analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like); anesthetics (e.g., cyclopropane, enflurane, halothane, isoflurane, methoxyflurane, nitrous oxide, propofol, and the like); antiasthmatics (e.g., Azelastine, Ketotifen, Traxanox, and the like); antibiotics (e.g., neomycin, streptomycin, chloramphenicol, cephalosporin, ampicillin, penicillin, tetracycline, and the like); antidepressants (e.g., nefopam, oxypertine, doxepin hydrochloride, amoxapine, trazodone hydrochloride, amitriptyline hydrochloride, maprotiline hydrochloride, pheneizine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like); antidiabetics (e.g., biguanides, hormones, sulfonylurea derivatives, and the like); antifungal agents (e.g., griseofulvin, keloconazole, amphotericin B, Nystatin, candicidin, and the like); antihypertensive agents (e.g., propanolol, propafenone, oxyprenolol, Nifedipine, reserpine, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, and the like); anti-inflammatories (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like); antineoplastics (e.g., adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxanes and derivatives thereof (e.g., paclitaxel and derivatives thereof, docetaxel and derivatives thereof, and the like), vinblastine, vincristine, tamoxifen, piposulfan, and the like); antianxiety agents (e.g., lorazepam, buspirone hydrochloride, prazeparn, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like); immunosuppressive agents (e.g., cyclosporine, azathioprine, mizoribine, FK506 (tacrolimus), and the like); antimigraine agents (e.g., ergotamine tartrate, propanolol hydrochloride, isometheptene mucate, dichloralphenazone, and the like); sedatives/hypnotics (e.g., barbiturates (e.g., pentobarbital, pentobarbital sodium, secobarbital sodium, and the like), benzodiazapines (e.g., flurazepam hydrochloride, triazolam, tomazeparm, midazolam hydrochloride, and the like), and the like); antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like), and the like); antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like); antimanic agents (e.g., lithium carbonate, and the like); antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like); antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like); antigout agents (e.g., colchicine, allopurinol, and the like); anticoagulants (e.g., heparin, heparin sodium, warfarin sodium, and the like); thrombolytic agents (e.g., urokinase, streptokinase, altoplase, and the like); antifibrinolytic agents (e.g., aminocaproic acid, and the like); hemorheologic agents (e.g., pentoxifylline, and the like); antiplatelet agents (e.g., aspirin, empirin, ascriptin, and the like); anticonvulsants (e.g., valproic acid, divalproate sodium, phenyloin, phenyloin sodium, clonazepam, primidone, phenobarbitol, phenobarbitol sodium, carbamazepine, amobarbital sodium, methsuximide, metharbital, mephobarbital, mephenyloin, phensuximide, paramethadione, ethotoin, phenacemide, secobarbitol sodium, clorazepate dipotassium, trimethadione, and the like); antiparkinson agents (e.g., ethosuximide, and the like); antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimeprazine tartrate, and the like); agents useful for calcium regulation (e.g., calcitonin, parathyroid hormone, and the like); antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like); antiviral agents (e.g., interferon gamma, zidovudine, amantadine hydrochloride, ribavirin, acyclovir, and the like); antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like); anti-infectives (e.g., GM-CSF, and the like); bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate, and the like), anticholinergic agents (e.g., ipratropium bromide, and the like), xanthines (e.g., aminophylline, dyphylline, metaproterenol sulfate, aminophylline, and the like), mast cell stabilizers (e.g., cromolyn sodium, and the like), inhalant corticosteroids (e.g., flurisolidebeclomethasone dipropionate, beclomethasone dipropionate monohydrate, and the like), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like); hormones (e.g., androgens (e.g., danazol, testosterone cypionate, fluoxymesterone, ethyltostosterone, testosterone enanthate, methyltestosterone, fluoxymesterone, testosterone cypionate, and the like), estrogens (e.g., estradiol, estropipate, conjugated estrogens, and the like), progestins (e.g., methoxyprogesterone acetate, norethindrone acetate, and the like), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium, and the like), and the like; hypoglycemic agents (e.g., human insulin, purified beef insulin, purified pork insulin, glyburide, chlorpropamide, glipizide, tolbutamide, tolazamide, and the like); hypolipidemic agents (e.g., clofibrate, dextrothyroxine sodium, probucol, lovastatin, niacin, and the like); proteins (e.g., DNase, alginase, superoxide dismutase, lipase, and the like); nucleic acids (e.g., sense or anti-sense nucleic acids encoding any therapeutically useful protein, including any of the proteins described herein, and the like); agents useful for erythropoiesis stimulation (e.g., erythropoietin, and the like); antiulcer/antireflux agents (e.g., famotidine, cimetidine, ranitidine hydrochloride, and the like); antinauseants/antiemetics (e.g., meclizine hydrochloride, nabilone, prochlorperazine, dimenhydrinate, promethazine hydrochloride, thiethylperazine, scopolamine, and the like); oil-soluble vitamins (e.g., vitamins A, D, E, K, and the like); as well as other drugs such as mitotane, visadine, halonitrosoureas, anthrocyclines, ellipticine, and the like.

Additional examples of pharmacologically active agents include those compounds which are substantially water insoluble and which are listed in the "Therapeutic Category and Biological Activity Index" of The Merck Index (12th Ed'n, 1996), the entire relevant contents of which are hereby incorporated by reference.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, and the like), as well as other diagnostic agents which cannot readily be delivered without some physical and/or chemical modification to accommodate the substantially water insoluble nature thereof.

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

In certain embodiments, the compositions of the present invention have the zeta potential between −20 mV and −50 mV. As indicated above, the zeta potentials in this range are desirable for improving the stability and safety of the compositions. This inventor discovered that compositions with a zeta potential between 0 to −20 mV are less stable compared to emulsions with zeta potential between −20 mV and −50 mV, whereas compositions with an excessively highly negative zeta potential (e.g., −60 mV to −70 mV) are more toxic in an animal model.

1. Oil-in-Water Emulsions

In one aspect, the present invention provides an oil-in-water emulsion for delivering a substantially water insoluble pharmacologically active agent.

An "oil-in-water emulsion" refers to a colloidal dispersion system in which liquid oil is dispersed in small droplets (the discrete phase) in an aqueous medium (the continuous phase).

In certain embodiments, the oil droplets of the oil-in-water emulsion comprise a substantial portion of a substantially water insoluble pharmacologically active agent. For example, in certain embodiments, in excess of about 80% of the pharmacologically active agent is dissolved and remains in the oil droplets. In certain embodiments, greater than about 85%, 90%, 92%, 94%, 95%, 96%, 97%, 98%, or 99% of the pharmacologically active agent is present in the oil phase. In certain embodiments, the oil droplets are free of crystalline solid at ambient temperature (e.g., at −4° C., 2-8° C., or 20-25° C.).

In certain embodiments, the ratio of a pharmacologically active agent to the oil component(s) is no less than about 1:100. In certain embodiments, the ratio is no less than about 1:90, 1:80, 1:70, 1:60, 1:50, 1:40, 1:30, 1:20, 1:10, or 1:5.

The presence of VES in the oil-in-water emulsion allows the oil droplets to be of smaller size. For example, in certain embodiments, the average diameter of the oil droplets is no greater than about 1 micron. In certain other embodiments, the average diameter of the oil droplets is no greater than about 500 nm, 400 nm, 300 nm, 200 nm, or 150 nm.

In certain embodiments, the oil-in-water emulsion is sterilized. For instance, the oil-in-water emulsion with an average oil droplet diameter of no more than about 200 nm may be sterilized via a 0.2 µm filter.

In certain embodiments, the oil-in-water emulsions comprise a substantially water insoluble pharmacologically active agent, VES (or its analogue or salt), at least one oil, phospholipid(s) and water.

The term "oil" is used herein in a general sense to identify hydrocarbon derivatives, carbohydrate derivatives, or similar organic compounds that are liquid at body temperatures, e.g., about 37° C., and are pharmacologically acceptable in injectable formulations. It includes glycerides or non-glycerides.

In certain embodiments, the oil in the emulsions of the present invention is or comprises a vegetable oil. "Vegetable oil" refers to oil derived from plant seeds or nuts. Exemplary vegetable oils include, but are not limited to, almond oil, borage oil, black currant seed oil, corn oil, safflower oil, soybean oil, sesame oil, cottonseed oil, peanut oil, olive oil, rapeseed oil, coconut oil, palm oil, canola oil, etc.

Vegetable oils are typically "long-chain triglycerides," formed when three fatty acids (usually about 14 to about 22 carbons in length, with unsaturated bonds in varying numbers and locations, depending on the source of the oil) form ester bonds with the three hydroxyl groups on glycerol. In certain embodiments, vegetable oils of highly purified grade (also called "super refined") are generally used to ensure safety and stability of oil-in-water emulsions. In certain embodiments, hydrogenated vegetable oils, which are produced by controlled hydrogenation of the vegetable oil, may be used in the present invention.

In certain embodiments, the oil in the oil-in-water emulsion is or comprises a medium chain triglyceride. "Medium chain triglycerides" (MCT's) are another class of triglyceride oil that can be either naturally derived or synthetic. MCT's are made from fatty acids that are usually about 8 to about 12 carbons in length. Like vegetable oils, MCT's have been used extensively in emulsions designed for injection as a source of calories, for patients requiring parenteral nutrition. Such oil is commercially available as Miglyol 812 from SASOL GmbH, Germany, CRODAMOL GTCC-PN from Croda Inc. of Parsippany, N.J., or Neobees M-5 oil from PVO International, Inc., of Boonton, N.J. Other low-melting medium chain oils may also be used in the present invention.

In certain embodiments, the oil in the oil-in-water emulsion of the present invention is or comprises animal fat. "Animal fat" refers to oil derived from an animal source. It also comprises triglycerides, but the lengths of, and unsaturated bonds in, the three fatty acid chains vary, compared to vegetable oils. Animal fats from sources that are solid at room temperature (such as tallow, lard, etc.) can be processed to render them liquid if desired. Other types of animal fats that are inherently liquid at room temperature include various fish oils, etc.

In certain embodiments, the combinations of vegetable oil and MCT oil are used in the present invention. Such combinations generally have long a record of safe use in combination in injectable emulsions and provide the superior stability for the colloidal dispersions or dry solid of this invention. The specific type of vegetable oil used (i.e., soy bean oil, corn oil, or safflower oil, etc.) is not critical, so long as it is safe, well tolerated, pharmaceutically acceptable, chemically stable and provides dispersion droplets having a desired size range.

The content of the total oil component in the emulsions (prior to being dried) of this invention may be within a range of about 1% to about 20%, by weight. In certain embodiments, the total concentration of the oil component is within a range of about 2% to about 15%, or about 5% to about 10%. In certain embodiments, the total concentration of the oil component is about, or at most about, 1%, 2%, 3%, 4%, 5%, 6%, 7%, 8%, 9%, 10%, 12%, 15%, 17%, or 20% by weight. In certain embodiments, the emulsions comprise oil in an amount that does not result in hyperlipidemia when administered to a subject.

In certain embodiments, the vegetable oil to MCT oil ratio in a colloidal suspension is within a range of about 5:1 to about 1:5, by weight. In certain embodiments, the ratio of the vegetable oil to MCT oil is within a range of about 2:1 to about 1:2. In certain embodiments, the ratio of the vegetable oil to MCT oil is about 5:1, 4:1, 3:1, 2:1, 1:1, 1:2, 1:3, 1:4 or 1:5.

The non-glycerides referred in this invention are mainly cholesterol and derivatives thereof.

In certain embodiments, the oil component of a formulation of the present invention comprises soybean oil and cholesterol.

In certain embodiments, the oil-in-water emulsion of the present invention comprises a phospholipid. A "phospholipid" refers to a triester of glycerol with two fatty acids and one phosphate ion. Exemplary phospholipids useful in the present invention include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The phospholipid component of the drug delivery composition can be either a single phospholipid or a mixture of several phospholipids. The phospholipids employed should be acceptable for the chosen route of administration.

The phospholipids useful in the present invention can preferably be of natural origin for enhanced safety. Naturally occurring phospholipids include soy lecithin, egg lecithin, hydrogenated soy lecithin, hydrogenated egg lecithin, sphingosine, gangliosides, and phytosphingosine and combinations thereof.

Naturally occurring lecithin is a mixture of the diglycerides of stearic, palmitic, and oleic acids, linked to the choline ester of phosphoric acid, commonly called phosphatidylcholine, and can be obtained from a variety of sources such as eggs and soya beans. Soy lecithin and egg lecithin (including hydrogenated versions of these compounds) have a long history of safety in biological systems, possess combined emulsification and solubilization properties, and tend to be broken down into innocuous substances more rapidly than most synthetic surfactants. Commercially available soya phospholipids are the Centrophase and Centrolex products marketed and sold by Central Soya, Phospholipon from Phospholipid GmbH, Germany, Lipoid by Lipoid GmbH, Germany, and EPIKURON by Degussa.

Hydrogenated lecithin is the product of controlled hydrogenation of lecithin. It may also be used in the present invention.

According to the United State Pharmacopoeia (USP), lecithin is a non-proprietary name describing a complex mixture of acetone-insoluble phospholipids, which consists chiefly of phosphotidylcholine, phosphotidylethanolamine, phosphotidylserine and phosphotidylinositol, combined with various amounts of other substances such as triglycerides, fatty acids, and carbohydrates.

Pharmaceutically, lecithins are mainly used as dispersing, emulsifying, and stabilizing agents and are included in intramuscular and intravenous injections, parenteral nutritional formulations and topical products. Lecithin is also listed in the FDA Inactive Ingredients Guide for use in inhalations, IM and IV injections, oral capsules, suspensions and tablets, rectal, topical, and vaginal preparations.

Phospholipids can also be synthesized and the common synthetic phospholipids are listed below:
Diacylglycerols
1,2-Dilauroyl-sn-glycerol (DLG)
1,2-Dimyristoyl-sn-glycerol (DMG)
1,2-Dipalmitoyl-sn-glycerol (DPG)
1,2-Distearoyl-sn-glycerol (DSG)
Phosphatidic Acids
1,2-Dimyristoyl-sn-glycero-3-phosphatidic acid, sodium salt (DMPA,Na)
1,2-Dipalmitoyl-sn-glycero-3-phosphatidic acid, sodium salt (DPPA,Na)
1,2-Distearoyl-sn-glycero-3-phosphatidic acid, sodium salt (DSPA,Na)
Phosphocholines
1,2-Dilauroyl-sn-glycero-3-phosphocholine (DLPC)
1,2-Dimyristoyl-sn-glycero-3-phosphocholine (DMPC)
1,2-Dipalmitoyl-sn-glycero-3-phosphocholine (DPPC)
1,2-Distearoyl-sn-glycero-3-phosphocholine (DSPC)
Phosphoethanolamines
1,2-Dilauroyl-sn-glycero-3-phosphoethanolamine (DLPE)
1,2-Dimyristoyl-sn-glycero-3-phosphoethanolamine (DMPE)
1,2-Dipalmitoyl-sn-glycero-3-phosphoethanolamine (DPPE)
1,2-Distearoyl-sn-glycero-3-phosphoethanolamine (DSPE)
Phosphoglycerols
1,2-Dilauroyl-sn-glycero-3-phosphoglycerol, sodium salt (DLPG)
1,2-Dimyristoyl-sn-glycero-3-phosphoglycerol, sodium salt (DMPG)
1,2-Dimyristoyl-sn-glycero-3-phospho-sn-1-glycerol, ammonium salt (DMP-sn-1-G,NH4)
1,2-Dipalmitoyl-sn-glycero-3-phosphoglycerol, sodium salt (DPPG,Na)
1,2-Distearoyl-sn-glycero-3-phosphoglycerol, sodium salt (DSPG,Na)
1,2-Distearoyl-sn-glycero-3-phospho-sn-1-glycerol, sodium salt (DSP-sn-1G,Na)
Phosphoserines
1,2-Dipalmitoyl-sn-glycero-3-phospho-L-serine, sodium salt (DPPS,Na)
Mixed Chain Phospholipids
1-Palmitoyl-2-oleoyl-sn-glycero-3-phosphocholine (POPC)
1-Palmitoyl-2-oleoyl-sn-glycero-3-phosphoglycerol, sodium salt (POPG,Na)
1-Palmitoyl-2-oleoyl-sn-glycero-3-phosphoglycerol, ammonium salt (POPG,NH4)
Lysophospholipids
1-Palmitoyl-2-lyso-sn-glycero-3-phosphocholine (P-lyso-PC)
1-Stearoyl-2-lyso-sn-glycero-3-phosphocholine (S-lyso-PC)
Pegylated Phospholipids
N-(Carbonyl-methoxypolyethyleneglycol 2000)-MPEG-2000-DPPE
1,2-dipalmitoyl-sn-glycero-3-phosphoethanolamine, sodium salt
N-(Carbonyl-methoxypolyethyleneglycol 5000)-MPEG-5000-DSPE
1,2-distearoyl-sn-glycero-3-phosphoethanolamine, sodium salt
N-(Carbonyl-methoxypolyethyleneglycol 5000)-MPEG-5000-DPPE
1,2-dipalmitoyl-sn-glycero-3-phosphoethanolamine, sodium salt
N-(Carbonyl-methoxypolyethyleneglycol 750)-MPEG-750-DSPE
1,2-distearoyl-sn-glycero-3-phosphoethanolamine, sodium salt
N-(Carbonyl-methoxypolyethyleneglycol 2000)-MPEG-2000-DSPE
1,2-distearoyl-sn-glycero-3-phosphoethanolamine, sodium salt The amount of phospholipids, by weight, in the emulsions (prior to being dried) of this invention may be within a range of about 1% to about 20%. In certain embodiments, the amount of phospholipids, by weight, may be within a range of about 5% to about 15%, or about 8% to about 12%. In certain embodiments, the amount of phospholipids is about 1%, 2%, 3%, 4%, 5%, 6%, 7%, 8%, 9%, 10%, 11%, 12%, 13%, 14%, 15%, 16%, 17%, 18%, 19% and 20%.

As described above, the oil-in-water emulsions comprise an aqueous medium. "Aqueous medium" or "aqueous phase" refers to a water-containing liquid which can contain pharmaceutically acceptable additives, such as acidifying, alkalizing, buffering, chelating, complexing and solubilizing agents, antioxidants and antimicrobial preservatives, suspending and/or viscosity modifying agents, tonicity modifying agent, cryo-protectant, and other biocompatible materials or therapeutic agents. In certain embodiments, such additives assist in stabilizing the colloidal dispersion or in rendering the formulations of the present invention biocompatible. In certain embodiments, the pH of the emulsion is about 5 to about 9 (e.g., about 6 to about 8).

The aqueous phase generally has an osmolality of approximately 300 to 1000 mOsm and may include potassium or sodium chloride, trahalose, sucrose, sorbitol, glycerol, mannitol, polyethylene glycol, propylene glycol, albumin, amino acid and mixtures thereof. In certain embodiments, an osmolality of about 300 mOsm is achieved with an agent that also increases osmotic pressure, such as dextrose, lactose, sorbitol or sucrose.

"Antioxidants" used in this invention refer to primarily metal ion chelator and/or reducing agents that are safe to use in an injectable product. A metal ion chelator works as an antioxidant by binding to metal ions and thereby reduces the catalytic effect of metal ion on the oxidation reaction of VES. Metal chelators that are useful in this invention may include EDTA, glycine and citric acid or salts thereof.

In certain embodiments, the concentration of disodium edetate in the colloidal dispersion of this invention can be from about 0.0001% to about 1% w/v. In certain embodiments, the concentration is from about 0.001% to about 0.1% w/v, or from about 0.001% to about 0.005% w/v.

In certain embodiments, the oil-in-water emulsions of the present invention do not contain any excipient that causes potentially life threatening hypersensitivity reactions, hemolysis or vein irritation, or other ingredients such as vitamin E TPGS, polysorbate 80, albumin, or oleic acid.

The reducing agents exhibit their antioxidant effect by reacting with oxidizing agents in competition with VES or by converting oxidized VES back to the original VES in the reduced form. The reducing agents useful in this invention include, but are not limited to, ascorbic acid or salts thereof, ascorbyl palmitate, sodium metabisulfite, propyl gallate, butylated hydroxyanisole, butylated hydroxytoluene, tocopherol, amino acids or salts thereof, citric acid or salts thereof, reducing sugars, or mixtures thereof.

In certain embodiments, the oil-in-water emulsions of the present invention further comprise a bulking agent. A "bulking agent" refers to a safe and biocompatible agent that protects the oil-in-water emulsion during drying by either a vacuum-drying, spray-drying or freeze-drying method by maintaining the discrete and sub-micron size droplets in the surrounding materials. The bulking agent of this invention also function as the main component of the continuous phase of the oil-in-solid composition resulted from the oil-in-water emulsion after removal of water.

The bulking agent useful for this invention include, but are not limited to, monosaccharide, disaccharide, polysaccharide, propylene glycol, polyethylene glycol, glycerol, polyol, dextrin, cyclodextrin, starch, cellulose and cellulose derivative, protein, peptide, amino acid, sodium chloride, polyvinylpyrrolidone, or mixtures thereof. For instance, in certain embodiments, the bulking agent is mannitol, sorbitol, xylitol, lactose, fructose, xylose, sucrose, trahalose, mannose, maltose, glucose, dextrose, dexstrane, or a mixture thereof. In certain embodiments, the bulking agent is sucrose, a combination of sucrose and mannitol, or a combination of sucrose and trehalose. In certain embodiments, the formulations of the present invention do not comprise acacia.

The concentration of bulking agent in the emulsion (prior to being dried) of this invention may be from about 5% to about 30% w/v. In certain embodiments, the concentration is from about 10% to about 25% w/v or from about 15% to 20% w/v.

In certain embodiments, the oil-in-water emulsion or its component(s) is injectable. "Injectable" refers to acceptance of an ingredient by a drug authority agent (e.g., the US FDA) by allowing it for use in an injection drug.

In certain embodiments, the oil-in-water emulsion or its component(s) is biocompatible. "Biocompatible" refers to the capability of performing functions within or upon a living organism in an acceptable manner, i.e., without undue toxicity or physiological or pharmacological effects.

In certain embodiments, the present invention provides the following exemplary oil-in-water emulsions:

1. an oil-in-water emulsion that comprises docetaxel or paclitaxel, VES, at least one injectable oil, injectable phospholipids and water, wherein the emulsion has a zeta potential between −20 mV and −50 mV, the average diameter of the said emulsion droplet is less than 200 nm, and the docetaxel- or paclitaxel-to-oil ratio is no less than 1:50 by weight.

2. an oil-in-water emulsion according to the first exemplary embodiment that comprises docetaxel or paclitaxel in a weight percentage concentration range of about 0.1 to about 1 (e.g., about 0.3 to about 0.8, and about 0.5 to about 0.7), vitamin E succinate in a weight percentage concentration range of about 0.01 to about 5 (e.g., about 0.1 to about 3 and about 0.2 to about 1), a vegetable oil in a weight percentage concentration range of 1 to 10 (about 2 to about 8 and about 3 to about 5), optionally a medium chain triglyceride oil in a weight percentage concentration range of about 1 to about 10 (about 2 to about 8 and about 3 to about 5), a phospholipid in a weight percentage concentration range of 1 to 20 (about 5 to about 15 and about 8 to about 12), optionally cholesterol in a weight percentage concentration range of about 0.01 to about 5 (about 0.1 to about 1 and about 0.4 to about 0.8), and water in a weight percentage concentration range of about 40 to about 90 (about 50 to about 90 and about 55 to about 85), and the pH of the emulsion is about 5 to 9.

3. an oil-in-water emulsion according to the second exemplary embodiment further comprising a bulking agent selected from dextrose, sucrose, lactose and a mixture thereof in a weight percentage concentration range of about 5 to about 50 (e.g., about 10 to about 40 and about 10 to about 20).

4. an oil-in-water emulsion comprising docetaxel or paclitaxel in a weight percentage concentration range of about 0.5 to about 0.7, VES in a weight percentage concentration of about 0.2 to about 1, a vegetable oil (e.g., soybean oil) in a weight percentage concentration range of about 3 to about 5, a medium chain triglyceride in a weight percentage concentration range of about 3 to about 5, a phospholipid (e.g., soy lecithin or egg lecithin) in a weight percentage concentration range of about 8 to about 12, cholesterol in a weight percentage concentration range of about 0.4 to about 0.8, and water in a weight percentage concentration range of about 55 to about 85.

5. an oil-in-water emulsion according to the fourth exemplary embodiment that further comprises a bulking agent (e.g., sucrose, dextrose, lactose, or a mixture thereof in a weight percentage concentration range of 10 to 20.

6. an oil-in-water emulsion that comprises docetaxel or paclitaxel in a weight percentage concentration range of about 0.1 to about 1.0 (e.g., about 0.4 to about 0.6), lecithin (e.g., soy lecithin or egg lecithin) in a weight percentage concentration range of about 5 to about 10, cholesterol in a weight percentage concentration range of about 1 to 1.5, VES in a weight percentage concentration range of about 0.2 to about 0.5, a bulking agent (e.g., sucrose, dextrose, lactose, or a mixture thereof in a weight percentage concentration range of about 10 to 20, and water.

7. an oil-in-water emulsion comprising docetaxel or paclitaxel in a weight percentage concentration range of about 0.1 to about 1, VES in a weight percentage concentration of about 0.2 to about 1, a vegetable oil (e.g., soybean oil) in a weight percentage concentration range of about 3 to about 5, a medium chain triglyceride in a weight percentage concentration range of about 3 to about 5, a phospholipid (e.g., soy lecithin or egg lecithin) in a weight percentage concentration range of about 8 to about 12, cholesterol in a weight percentage concentration range of about 0.4 to about 0.8, and water.

8. an oil-in-water emulsion according to the seventh exemplary embodiment that further comprises a bulking agent (e.g., sucrose, dextrose, lactose, or a mixture thereof in a weight percentage concentration range of 10 to 20.

9. an oil-in-water emulsion comprising 17-allylamino geldanamycin, combrestatin, camptothecin, thalidomide, itraconazole, amphotericin, or vericonazole in a weight percentage concentration range of about 0.1 to about 1.0, VES in a weight percentage concentration of about 0.2 to about 1, a vegetable oil (e.g., soybean oil) in a weight percentage concentration range of about 3 to about 5, a medium chain triglyceride in a weight percentage concentration range of about 3 to about 5, a phospholipid (e.g., soy lecithin or egg lecithin) in a weight percentage concentration range of about 8 to about 12, cholesterol in a weight percentage concentration range of about 0.4 to about 0.8, and water.

10. an oil-in-water emulsion according to the ninth exemplary embodiment that further comprises a bulking agent (e.g., sucrose, dextrose, lactose, or a mixture thereof) in a weight percentage concentration range of 10 to 20.

The oil-in-water emulsions of the present invention may be formed by a "double-homogenization technique" comprising the following steps:

(1) homogenizing an aqueous suspension of VES to form a submicron suspension of VES—the first homogenization process, (2) dissolving a pharmacologically active agent such as docetaxel in an oil phase comprising one or more oil and phospholipids. The step can be accomplished by vigorously agitating the mixture using an high shear equipment such as an IKA rotor-stator type of high-shear mixer, or optionally, by using ethanol as a solvent to dissolve the solid components first, combining all liquid components by mixing to form one uniform ethanolic solution containing the pharmacologically active agent, oil and phospholipid and finally removing the ethanol by vacuum drying, (3) combining the VES suspension and the oil phase, and optionally other components such as a bulking agent and agitate the mixture to form a crude oil-in-water emulsion, (4) passing the crude emulsion through a high pressure homogenizer such as a microfluidizer to form a submicron emulsion—the second homogenization process, and (5) passing the submicron emulsion through a 0.2 micron filter to sterilize the emulsion.

In certain embodiments, the first homogenization process may be performed by subjecting a crude suspension of VES in water to a high-pressure homogenization process using a microfluidizer operating at a predetermined pressure in the range of about 10,000 psi up to about 30,000 psi to form the submicron suspension of VES.

In certain embodiments, the second homogenization process may be performed by subjecting a mixture of the submicron VES suspension and an oil phase containing the pharmacologically active agent to a high-pressure homogenization process using a microfluidizer operating at a predetermined pressure in the range of about 10,000 psi up to about 30,000 psi, to form a submicron emulsion with droplets in a range of about 100 nm to about 300 nm, such as in a range of about 100 nm to about 200 nm, and in a range of about 100 nm to about 180 nm.

Additional description of preparing exemplary oil-in-water emulsions may be found in the examples.

2. Solid Compositions

In another aspect, the present invention provides a solid composition that comprises a substantially water insoluble pharmacologically active agent (e.g., docetaxel), is substantially free of water, and is prepared by removal of water from the emulsions as described above. The VES-stabilized oil-in-water emulsions of the present invention are sufficiently stable so that they can be dried to be substantially free of water to prevent hydrolysis of water insoluble pharmacologically active agents (e.g., docetaxel). The solid composition can be rehydrated with water to form an emulsion suitable of injection, and the average diameter of the re-formed emulsion droplets is no greater than about 1 micron. In certain embodiments, the average diameter of the re-formed emulsion droplets is no greater than about 500 nm, 400 nm, 300 nm, 200 nm, or 150 nm.

In certain embodiments, the solid composition comprises docetaxel in a weight percentage concentration range of about 0.2 to about 3 (e.g., about 0.8 to about 2.5 and about 1.3 to about 2.0), vitamin E succinate in a weight percentage concentration range of about 0.1 to about 12 (about 0.4 to about 9 and about 0.7 to about 7), a vegetable oil in a weight percentage concentration range of about 1.1 to about 21.9 (about 5.5 to about 16.4 and about 8.8 to about 13.2), optionally a medium chain triglyceride oil in a weight percentage concentration range of about 1.1 to about 21.9 (about 5.5 to about 16.4 and about 8.8 to about 13.2), a phospholipid in a weight percentage concentration range of about 2.7 to about 54.8 (about 13.7 to about 41.1 and about 21.9 to about 32.9), optionally cholesterol in a weight percentage concentration range of about 0.2 to about 3.3 (about 0.8 to about 2.5 and about 1.3 to about 2.0), and a bulking agent selected from dextrose, sucrose, lactose, and a mixture thereof in a weight percentage concentration range of about 4.7 to about 93.2 (e.g., about 23.3 to about 69.9 and about 37.3 to about 55.9).

In certain embodiments, the solid composition comprises docetaxel in a weight percentage concentration range of about 1.3 to about 2.0, vitamin E succinate in a weight percentage concentration range of about 0.7 to about 1.0, a vegetable oil (e.g., soybean oil) in a weight percentage concentration range of about 8.8 to about 13.2, a medium chain triglyceride oil in a weight percentage concentration range of about 8.8 to about 13.2, a phospholipid (e.g., soy lecithin or egg lecithin) in a weight percentage concentration range of about 21.9 to about 32.9, cholesterol in a weight percentage concentration range of about 1.3 to about 2.0, and a bulking agent selected from dextrose, sucrose, lactose, and a mixture thereof in a weight percentage concentration range of about 37.3 to about 55.9.

The solid compositions may be prepared by dehydrating the above-described oil-in-water emulsions, such as by vacuum drying, freeze drying, or spray drying.

3. Suspension

In another aspect, the present invention provides a suspension composition comprising submicron solid particles of an amorphous or crystalline pharmacologically active agent, dispersed in an aqueous medium and stabilized by VES, wherein the solid particles are substantially free of liquid oil (e.g. vegetable oil or MCT), have an average diameter of less than 200 nm and a zeta potential between −20 mV and −50 mV. In certain embodiments, the suspension that comprises docetaxel or paclitaxel in a weight percentage concentration range of about 0.1 to about 1.0 (e.g., about 0.4 to about 0.6), lecithin (e.g., soy lecithin or egg lecithin) in a weight percentage concentration range of about 5 to about 15, cholesterol in a weight percentage concentration range of about 0.5 to about 2, VES in a weight percentage concentration range of about 0.1 to about 5, a bulking agent (e.g., sucrose, dextrose, lactose, or a mixture thereof in a weight percentage concentration range of about 10 to about 20, and water.

In another aspect, a solid composition may be prepared by dehydrating the above-described suspension, such as by vacuum drying, freeze drying, or spray drying.

In certain embodiments, the solid composition prepared from a suspension comprises docetaxel in a weight percentage concentration range of about 1.3 to about 2.0, vitamin E succinate in a weight percentage concentration range of about 1 to about 15, a phospholipid (e.g., soy lecithin or egg lecithin) in a weight percentage concentration range of about 22 to about 32, cholesterol in a weight percentage concentration range of about 1 to about 5, and a bulking agent selected from dextrose, sucrose, lactose, and a mixture thereof in a weight percentage concentration range of about 35 to about 75.

The suspension of the present invention may be formed by the "double-homogenization technique" comprising the following steps:

(1) homogenizing an aqueous suspension of VES to form a submicron suspension of VES—the first homogenization process, (2) dissolving a pharmacologically active agent such as docetaxel, phospholipids and cholesterol in ethanol to form one uniform ethanolic solution and removing the ethanol by vacuum drying to produce a solid mass, (3) combining the VES suspension and the solid mass, water and optionally other components such as a bulking agent and agitate the mixture to form a crude suspension, (4) passing the crude suspension through a high pressure homogenizer such as a microfluidizer to form a submicron suspension—the second homogenization process, and (5) passing the submicron suspension through a 0.2 micron filter to sterilize the suspension.

In certain embodiments, the first homogenization process may be performed by subjecting a crude suspension of VES in water to a high-pressure homogenization process using a microfluidizer operating at a predetermined pressure in the range of about 10,000 psi up to about 30,000 psi to form the submicron suspension of VES.

In certain embodiments, the second homogenization process may be performed by subjecting a mixture of the submicron VES suspension and an solid mass containing the pharmacologically active agent to a high-pressure homogenization process using a microfluidizer operating at a predetermined pressure in the range of about 10,000 psi up to about 30,000 psi, to form a submicron suspension with particles in a range of about 100 nm to about 300 nm, such as in a range of about 100 nm to about 200 nm, and in a range of about 100 nm to about 180 nm.

B. Methods for Using VES-Stabilized Compositions

In a related aspect, the present invention provides a method of treating carcinomas comprising administering the VES-stabilized emulsions that comprise an anti-cancer agent (e.g., docetaxel or paclitaxel) to a subject in need of such a treatment. The VES-stabilized emulsion may be administered to animals or humans via intravascular, oral, intramuscular, cutaneous and subcutaneous routes. Other routes of administration include, but are not limited to, intraabdominal, intraarterial, intraarticular, intracapsular, intracervical, intracranial, intraductal, intradural, intralesional, intralocular, intralumbar, intramural, intraocular, intraoperative, intraparietal, intraperitoneal, intrapleural, intrapulmonary, intraspinal, intrathoracic, intratracheal, intratympanic, intrauterine, and intraventricular. The VES-stabilized emulsions of the present invention may also be nebulized using suitable aerosol propellants, which are known in the art for pulmonary delivery of lipophilic compounds. The VES-stabilized emulsions may be administered by instillation in a form of ophthalmic drops.

In another aspect, the present invention provides a method of treating other diseases comprising administering the VES-stabilized compositions that comprise a pharmacologically active agent effective in treating the other diseases to a subject in need of such a treatment. The VES-stabilized emulsion may be administered to animals or humans via any route appropriate for the particular treatment known in the art, including those described above for treating cancer. The diseases that may be treated by the compositions of the present invention include, but are not limited to, infection (e.g., microbial, viral, fungal infections), inflammation, allergy, arrhythmia, depression, hypertension, diabetes, lipid disorders, immune system disorders, metabolism disorders, and homological disorders.

For example, in one embodiment, the present invention provides a method for treating fungal infection comprising administering a VES-stabilized composition that comprises an antifungal agent (e.g., itraconazole, amphotericin, and vericonazole) to a subject in need of such a treatment.

The general principles of the present invention may be more fully appreciated by reference to the following non-limiting examples. As shown in the examples, certain VES stabilized oil-in-water emulsions that comprise docetaxel according to the present invention are non-allergenic, less toxic than, but as efficacious as, the marketed product TAXOTERE™, non-irritant at the injection site, and physically and chemically stable.

EXAMPLES

Example 1

A VES-stabilized docetaxel emulsion (Table 1.1) was prepared as in a composition as described below.

TABLE 1.1

| Component | % w/w |
|---|---|
| Docetaxel | 0.6 |
| Medium chain triglyceride, EP | 4 |
| Soybean Oil, USP | 4 |
| Soy lecithin, USP/EP | 10 |
| Cholesterol, NF | 0.6 |

TABLE 1.1-continued

| Component | % w/w |
| --- | --- |
| Vitamin E Succinate, USP | 0.3 |
| Sucrose, NF | 17.5 |
| De-ionized water, qs to | 100 |

The VES-stabilized emulsion was prepared by the double-homogenization technique, comprising (1) Preparation of a 5% VES submicron suspension by a microfluidizer (Model 110F by microfluidics) equipped with an emulsion interaction chamber at an operation pressure of 10,000-23,000 psi.

(2) Preparation of the oil phase by combining and mixing docetaxel, soybean oil, medium chain triglyceride, egg lecithin and sufficient amount of ethanol to form a clear yellow solution. The solution was dried under vacuum using a rotary evaporator until the residual ethanol content is less than 2% of the combined weight of the other components to obtain a thick yellow liquid (i.e., the oil phase).

(3) Preparation of a crude emulsion by combining and mixing the VES suspension, oil phase, sucrose and water using a high shear mixer (e.g. Ultra Turrax by Tekmar Company.

(4) Preparation of a submicron emulsion by passing the crude emulsion through a microfluidizer (Model 110F by microfluidics) equipped with an emulsion interaction chamber at an operation pressure of 10,000-23,000 psi until droplet size reached below 200 nm. The resulting emulsion was filtered through a sterile 0.2 micron filter, and the filtered emulsion was then filled into glass vials, The final VES-stabilized emulsion was a translucent off-white liquid.

(5) Preparation of a dry composition by freeze-drying the emulsion in Step 4 to obtain an off-white "cake" in vials, which was easily reconstituted with water to re-generate a translucent off-white emulsion.

The average droplet size of the reconstituted emulsion is measured to be 124 nm by a laser light scattering spectrometer (Model 370 Submicron Particle Sizer by Particle Sizing System, Santa Barbara, Calif.). The docetaxel concentrations in the emulsion were determined to be 6.64 mg/mL by a reversed phase high-pressure liquid chromatography (Hewlett Packard Model 1050 HPLC). The drug-to-oil ratio was 1:14 and the zeta potential was measured to be −41 mV using a Zeta potential instrument (Malvern Zetasizer Nano model).

Conclusion: a VES-stabilized emulsion having a small droplet size (<200 nm), a high drug-to-oil ratio (1:14) and a desired zeta potential of −41 mV was prepared by the double homogenization technique.

Example 2

Another VES-stabilized docetaxel emulsion (Table 1.2) was prepared using the same double homogenization technique as described in Example 1.

TABLE 1.2

| Component | % w/w |
| --- | --- |
| Docetaxel | 0.6 |
| Medium chain triglyceride, EP | 4 |
| Soybean Oil, USP | 4 |
| Egg lecithin, USP/EP | 10 |
| Cholesterol, NF | 0.6 |
| Vitamin E Succinate, USP | 0.3 |

TABLE 1.2-continued

| Component | % w/w |
| --- | --- |
| Sucrose, NF | 17.5 |
| De-ionized water, qs to | 100 |

The average droplet size of the reconstituted emulsion is measured to be 208 nm by a laser light scattering spectrometer (Model 370 Submicron Particle Sizer by Particle Sizing System, Santa Barbara, Calif.). The docetaxel concentrations in the emulsion were determined to be 6.48 mg/mL by a reversed phase high-pressure liquid chromatography (Hewlett Packard Model 1050 HPLC). The drug-to-oil ratio was 1:14 and the zeta potential was measured to be −38 mV using a Zeta potential instrument (Malvern Zetasizer Nano model).

Conclusion: another VES-stabilized emulsion having a small droplet size (208 nm), a high drug-to-oil ratio (1:14) and a desired zeta potential of −38 mV was prepared by the double homogenization technique.

Example 3

Yet another VES-stabilized docetaxel emulsion (Table 1.3) was prepared using the same double homogenization technique as described in Example 1.

TABLE 1.3

| Component | % w/w |
| --- | --- |
| Docetaxel | 0.3 |
| Medium chain triglyceride, EP | 2 |
| Soybean Oil, USP | 2 |
| Egg lecithin, USP/EP | 5 |
| Cholesterol, NF | 0.3 |
| Vitamin E Succinate, USP | 3.5 |
| Sucrose, NF | 15 |
| De-ionized water, qs to | 100 |

The average droplet size of the reconstituted emulsion is measured to be 87 nm by a laser light scattering spectrometer (Model 370 Submicron Particle Sizer by Particle Sizing System, Santa Barbara, Calif.). The docetaxel concentrations in the emulsion were determined to be 3.02 mg/mL by a reversed phase high-pressure liquid chromatography (Hewlett Packard Model 1050 HPLC). The drug-to-oil ratio was 1:14 and the zeta potential was measured to be −69 mV using a Zeta potential instrument (Malvern Zetasizer Nano model).

Conclusion: a VES-stabilized emulsion having a small droplet size (87 nm), a high drug-to-oil ratio (1:14) and an exceedingly high zeta potential of −69 mV was prepared by the double homogenization technique. This lot was found to be more toxic than other VES-stabilized emulsions.

Example 4

A paclitaxel emulsion (without VES) was prepared according to US Patent Application Publication No. 20030099674 to contain the following:

| Component | % w/w |
| --- | --- |
| Paclitaxel | 0.05 |
| Medium chain triglyceride, EP | 1.55 |

| Component | % w/w |
|---|---|
| Soybean Oil, USP | 1.55 |
| Egg lecithin, USP/EP | 5 |
| Sucrose, NF | 15 |
| De-ionized water, qs to | 100 |

The average droplet size of the emulsion is measured to be 115 nm by a laser light scattering spectrometer (Model 370 Submicron Particle Sizer by Particle Sizing System, Santa Barbara, Calif.). The drug-to-oil ratio was 1:62 and the zeta potential was measured to be −14 mV using a Zeta potential instrument (Malvern Zetasizer Nano model).

Conclusion: This emulsion is physically less stable than the VES-stabilized emulsions in Examples 1, 2 and 3 upon freeze-drying.

Example 5

Studies were conducted to evaluate the stability of docetaxel (chemical stability) in the VES-stabilized emulsions and the stability of the emulsions themselves (physical stability) according to Examples 1, 2 and 3. The chemical stability was determined based on concentration and purity of docetaxel in the emulsion over time. The docetaxel concentration and purity in the emulsion were determined by a reversed phase high-pressure liquid chromatography (Hewlett Packard Model 1050 HPLC). The physical stability was evaluated based on the average oily droplet diameter. The average oil droplet diameter was measured using a laser light scattering spectrometer (Model ZEN3600, Zeta sizer Nano series by Malvern).

Batch No. 1 (Prepared According to Example 3)

| Storage Condition | Docetaxel Concentration (mg/mL) by HPLC | | | | |
|---|---|---|---|---|---|
| | Initial | 1 month | 3 month | 5 month | 12 month |
| −20° C. | 3.02 | 2.99 | 3.02 | 2.99 | 3.04 |
| 5° C. | | 3.01 | 3.02 | 2.99 | 3.04 |
| 25° C. | | 2.98 | 2.96 | 2.93 | 2.72 |
| 30° C. | | 2.97 | 2.80 | N/A | N/A |
| 40° C. | | N/A | N/A | N/A | N/A |

| Storage Condition | Purity of Docetaxel (Peak area %) by HPLC | | | | |
|---|---|---|---|---|---|
| | Initial | 1 month | 3 month | 5 month | 12 month |
| −20° C. | 89.9 | 98.5 | 95.5 | 97.8 | 97.0 |
| 5° C. | | 96.9 | 94.9 | 96.3 | 97.1 |
| 25° C. | | 96.5 | 94.0 | 95.6 | 94.5 |
| 30° C. | | 95.0 | 95.3 | N/A | N/A |
| 40° C. | | N/A | N/A | N/A | N/A |

| Storage Condition | Average Droplet Diameter by Laser Light Scattering Measurement (nm) | | | | |
|---|---|---|---|---|---|
| | Initial | 1 month | 3 month | 5 month | 12 month |
| −20° C. | 87 | 86.3 | 85.3 | 85.8 | 82.5 |
| 5° C. | | 85.2 | 86.7 | 87.1 | 83.0 |
| 25° C. | | 83.5 | 91.0 | 100.1 | 168.8 |
| 30° C. | | 106.2 | N/A | N/A | N/A |
| 40° C. | | N/A | N/A | N/A | N/A |

Batch No. 2 (Prepared According to Example 3)

| Storage Condition | Docetaxel Concentration (mg/mL) by HPLC | | | |
|---|---|---|---|---|
| | Initial | 1 month | 4 month | 6 month |
| −20° C. | 3.14 | N/A | 3.21 | 3.20 |
| 5° C. | | N/A | 3.23 | 3.15 |
| 25° C. | | N/A | 3.24 | 3.06 |
| 30° C. | | N/A | 2.62 | 3.00 |
| 40° C. | | N/A | N/A | N/A |

| Storage Condition | Purity of Docetaxel (Peak area %) by HPLC | | | |
|---|---|---|---|---|
| | Initial | 1 Month | 4 month | 6 month |
| −20° C. | 99.1 | N/A | 97.9 | 96.1 |
| 5° C. | | N/A | 97.7 | 96.0 |
| 25° C. | | N/A | 97.6 | 96.8 |
| 30° C. | | N/A | 79.9 | 94.3 |
| 40° C. | | N/A | N/A | N/A |

| Storage Condition | Average Droplet Diameter by Laser Light Scattering Measurement (nm) | | | |
|---|---|---|---|---|
| | Initial | 1 month | 4 month | 6 month |
| −20° C. | 93.0 | N/A | 93.2 | 93.1 |
| 5° C. | | N/A | 95.3 | 92.0 |
| 25° C. | | N/A | 112.2 | 133.8 |
| 30° C. | | N/A | 197.6 | 307.7 |
| 40° C. | | N/A | N/A | N/A |

Batch No. 3 (Prepared According to Example 2)

| Storage Condition | Docetaxel Concentration (mg/vial) by HPLC | | |
|---|---|---|---|
| | Initial | 1 month | 3 month |
| 5° C. | 1.62 | 1.42 | 1.61 |
| 25° C. | | 1.27 | 1.50 |
| 30° C. | | 1.31 | 1.55 |
| 40° C. | | 1.49 | 1.52 |

| Storage | Purity of Docetaxel (Peak area %) by HPLC | | |
| --- | --- | --- | --- |
| Condition | Initial | 1 month | 3 month |
| 5° C. | 88.1 | 77.0 | 99.3 |
| 25° C. | | 72.3 | 99.4 |
| 30° C. | | 73.7 | 97.0 |
| 40° C. | | 77.1 | 97.0 |

| Storage | Average Droplet Diameter by Laser Light Scattering Measurement (nm) | | |
| --- | --- | --- | --- |
| Condition | Initial | 1 month | 3 month |
| 5° C. | 208 | 213 | 185.1 |
| 25° C. | | 228 | 172.0 |
| 30° C. | | 286 | 169.9 |
| 40° C. | | 315 | 252.7 |

Batch No. 4 (Prepared According to Example 1)

| Storage | Docetaxel Concentration (mg/vial) by HPLC | | | | |
| --- | --- | --- | --- | --- | --- |
| Condition | Initial | 1 month | 3 month | 6 month | 12 month |
| 5° C. | 1.66 | 1.59 | 1.61 | 1.67 | 1.59 |
| 25° C. | | 1.60 | 1.58 | 1.61 | 1.62 |
| 40° C. | | 1.58 | 1.53 | 1.57 | N/A |

| Storage | Purity of Docetaxel (Peak area %) by HPLC | | | | |
| --- | --- | --- | --- | --- | --- |
| Condition | Initial | 1 month | 3 month | 6 month | 12 month |
| 5° C. | 99.5 | 96.6 | 99.1 | N/A | 98.0 |
| 25° C. | | 95.4 | 99.3 | N/A | 97.4 |
| 40° C. | | 93.9 | 95.7 | N/A | N/A |

| Storage | Average Droplet Diameter by Laser Light Scattering Measurement (nm) | | | | |
| --- | --- | --- | --- | --- | --- |
| Condition | Initial | 1 month | 3 month | 6 month | 12 month |
| 5° C. | 124 | 119 | 123.4 | 130.7 | 122.0 |
| 25° C. | | 125 | 143.5 | 151.6 | 127.0 |
| 40° C. | | 223 | 200.9 | 282.2 | N/A |

Conclusion: Multiple lots of VES-stabilized emulsions according to this invention were tested and found to be physically and chemically stable at 5° C. or 25° C.

Example 6

Acute Toxicity Evaluation of a Novel Docetaxel Emulsion in Mice

AIM: To determine if acute toxic reactions occur in mice after receiving the VES-stabilized emulsion formulation of docetaxel according to Example 1, intravenously and to compare the toxicity with TAXOTERE™ (TX) formulation, which is the currently marketed formulation containing an allergenic solubilizer polysorbate 80.

METHODS: ICR mice were injected with the VES-stabilized emulsion formulation of docetaxel in the tail vein on Day 1 and observed for 14 days for toxicity. After 14 days the mice were sacrificed, weighed and morphologically examined for organ toxicity. The VES-stabilized emulsion formulation of docetaxel was reconstituted to 3 mg/mL, which is about 10 times the docetaxel concentration used clinically, and administered at the maximum dosing volume (0.4 mL per injection).

RESULTS: At the maximum injectable dose for mice (120 mg/kg), the VES-stabilized emulsion formulation of docetaxel did not show signs of acute toxicity, weight loss or morphological alteration in organs in the mice within 14 days after injection.

CONCLUSION: Based on these results the Highest Non-toxicity Tolerated Dose or HNTD, the US NCI's definition for this VES-stabilized emulsion formulation of docetaxel is estimated at $\geq 120$ mg/kg (360 mg/m$^2$) in mice. The published mouse HNTD for docetaxel in the TAXOTERE™ formulation is <285 mg/m$^2$ and the recommended human dose of TAXOTERE™ is 60-100 mg/m$^2$. This study suggests that the VES stabilized emulsion formulation is at least as safe in mice as the TAXOTERE™ formulation and may be better tolerated.

Example 7

Hypersensitivity Study of a New Docetaxel Lyophile Emulsion in Guinea Pigs

AIM: To evaluate hypersensitivity reaction as a part of systemic safety study of a VES-stabilized emulsion formulation of docetaxel according to this invention.

METHOD: Using guinea pigs to test the formulation hypersensitivity at two sensitizing dose levels: 1.5 mg/kg and 0.5 mg/kg (which is equivalent to the maximum human clinical daily dose of docetaxel) given intraperitoneally. In parallel, a 0.9% NaCl solution (normal saline) was used as a negative control and bovine albumin protein (2.5 mg/animal) as a positive control.

RESULTS: Ten days after the last intraperitoneal sensitization with the test articles, the guinea pigs were challenged by administering intravenously with the 2 folds dose of the VES stabilized emulsion formulation according to Example and observed for one hour. No animals sensitized and challenged with this VES-stabilized emulsion formulation of docetaxel showed any sign of allergic reaction.

CONCLUSION: The VES-stabilized emulsion formulation of docetaxel according to this invention did not cause any hypersensitivity reaction test animals and is non-allergenic.

Example 8

Docetaxel Emulsion Efficacy in Mouse S180 Sarcoma Model

AIM: To compare the anticancer activity of a VES-stabilized emulsion formulation of docetaxel according to Example 1 that does not contain polysorbate 80 to the currently marketed formulation, TAXOTERE™ (TX) containing polysorbate 80 in a mouse S180 sarcoma tumor model.

METHODS: Male and female ICR mice were inoculated subcutaneously with S180 sarcoma cells. Every other day for 9 days mice received the test article by intravenous injection followed by sacrifice and removal of tumor for weight determination. Percentage of tumor inhibition was calculated as the anticancer efficacy indicator. The experiment was repeated to establish reproducibility.

RESULTS: In the first experiment, a negative control group (received normal saline) produced a tumor weight of 1.48±0.50 g, the positive control group TX 10 mg/kg and the VES stabilized emulsion formulation of docetaxel treatment groups received three different doses at 5 mg/kg, 10 mg/kg, 20 mg/kg. Tumor weights of 0.68±0.26 g, 0.88±0.28 g, 0.49±0.22 g, and 0.26±0.11 g, respectively were obtained. Compared to the negative control group, a significant reduction in tumor was observed with % tumor inhibition at 54.2%, 40.1%, 66.5% and 82.4%, respectively. Compared to the positive control group, the 10 and 20 mg/kg VES stabilized emulsion formulation of docetaxel groups exhibited further tumor reduction with the 20 mg/kg group being statistically significantly different from the TX 10 mg/kg group. The second experiment resulted in tumor weights of 1.55±0.50 g for the negative control and 0.76±0.15 g, 0.95±0.25 g, 0.61±0.24 g, 0.42±0.14 g for the positive control, VES stabilized emulsion formulation 5 mg/kg, VES stabilized emulsion formulation 10 mg/kg, VES stabilized emulsion formulation 20 mg/kg, respectively. Compared to the negative control, statistically significant tumor inhibition was observed with % tumor inhibition of 51.2%, 38.9%, 60.4% and 72.8% for the positive control, VES stabilized emulsion formulation 5 mg/kg, VES stabilized emulsion formulation 10 mg/kg, VES stabilized emulsion formulation 20 mg/kg, respectively. Compared to the positive control, additional tumor reduction was observed with the VES stabilized emulsion formulation 20 mg/kg and VES stabilized emulsion formulation 10 mg/kg groups. The % tumor inhibition value of VES stabilized emulsion formulation 20 mg/kg is statistically different from that of 10 mg/kg TX formulation group.

CONCLUSION: The VES stabilized emulsion formulation exhibited significant anticancer activity reproducibly, in a dose dependent fashion, against mouse S180 sarcoma in ICR mice. This VES stabilized emulsion formulation is at least as efficacious as the TAXOTERE™ formulation.

Example 9

Anticancer Activity of Docetaxel Emulsion Lyophile in Mouse H22 Hepatoma Model

AIM: To evaluate anticancer activity of the VES-stabilized emulsion formulation of docetaxel according to Example 1 in mouse H22 hepatoma model.

METHOD: Male and female ICR mice were inoculated subcutaneously with H22 hepatoma cells, received every other day a test article by intravenous injection through tail veins for 9 days, sacrificed for removal of tumor for weigh determination. Percentage tumor inhibition was calculated as the anticancer efficacy indicator. The experiment was repeated for reproducibility.

RESULTS: In the first experiment, the negative control group (received normal saline) produced cancer weight of 1.261±0.255 g the positive control group (received a TAXOTERE™ formulation (TX) at 10 mg/kg) and the VES stabilized emulsion formulation treatment group at 5 mg/kg, 10 mg/kg, 20 mg/kg dose levels had tumor weights of 0.56±0.24 g, 0.69±0.19 g, 0.51±0.15 g, and 0.33±0.08 g, respectively. Compared to the negative control group, a significant reduction in tumor was obtained with % tumor inhibition at 51.7%, 40.0%, 56.0% and 71.5%, respectively. Compared to the positive control group, the 10 and 20 mg/kg VES stabilized emulsion formulation groups exhibited further tumor reduction with the 20 mg/kg VES stabilized emulsion formulation. The second experiment resulted in tumor weights of 1.08±0.26 g for the negative control and 0.60±0.17 g, 0.74±0.10 g, 0.55±0.19 g, 0.38±0.09 g for the positive control, VES stabilized emulsion formulation 5 mg/kg, VES stabilized emulsion formulation 10 mg/kg, and VES stabilized emulsion formulation 20 mg/kg, respectively. Compared to the negative control, statistically significant tumor inhibition was observed with % tumor inhibition of 44.5%, 31.5%, 49.5% and 64.2% for the positive control, VES stabilized emulsion formulation 5 mg/kg, VES stabilized emulsion formulation 10 mg/kg, and VES stabilized emulsion formulation 20 mg/kg, respectively. Compared to the positive control, additional tumor reduction was observed for the VES stabilized emulsion formulation 20 mg/kg and VES stabilized emulsion formulation 10 mg/kg groups. The % tumor inhibition value of the VES stabilized emulsion formulation 20 mg/kg is statistically different from that of 10 mg/kg TAXOTERE™ formulation group.

CONCLUSION: The VES-stabilized emulsion formulation of docetaxel according to this invention exhibited reproducibly significant anticancer activity, in a dose dependent fashion, against in mouse H22 hepatoma in ICR mice. This VES stabilized emulsion formulation is at least as efficacious as the TAXOTERE™ formulation at 10 mg/kg.

Example 10

Docetaxel Emulsion Efficacy in Nude Mice Xenografted with MDAMB-435 Human Breast Cancer AIM: To compare the anticancer activity of a VES-stabilized emulsion formulation of docetaxel according to this invention that does not contain polysorbate 80 to the currently marketed formulation, TAXOTERE™ (TX) containing polysorbate 80 in a xenografted MDAMB-435 human breast cancer model.

METHODS: Female nude mice (Balb/c) were inoculated with MDAMB-435 human breast cancer cells and allowed to grow the tumor to 100-200 mm$^3$ before receiving treatment. Every three days the mice received the test article for a total of 4 doses by intravenous injection via tail veins, measured from body weight and tumor volume. After 25 days, the animals were sacrificed and tumor volume and weight were determined. Relative tumor volume (RTV), relative tumor growth rate (T/C) and Percentage of tumor inhibition were calculated as the anticancer efficacy indicators for statistical analysis.

RESULTS: No significant body weight change was observed in the negative control group (received normal saline), and groups received 5 mg/kg and 10 mg/kG VES stabilized emulsion formulation whereas the groups received 10 mg/kg TX and 20 mg/kg VES stabilized emulsion formulation had significant body weight loss. No death in any group during the study. Compared to the negative control group, the VES stabilized emulsion formulation (20, 10 and 5 mg/kg) groups and TX 10 mg/kg group exhibited significant tumor volume reduction 10 days after the treatment (P<0.01-0.001). The RTV was 7.2 for the negative control group. For the VES stabilized emulsion formulation 20 mg/kg, VES stabilized emulsion formulation 10 mg/kg, VES stabilized emulsion formulation 5 mg/kg and TX 10 mg/kg groups, RTV were 0.16, 0.24, 1.8 and 0.23, T/C were 2.2%, 3.4%, 25% and 3.2%, average tumor weight (after 25 days) were 0.012 g, 0.028 g, 0.22 g and 0.024 g, and percentage of tumor inhibition were 98.5, 96.4, 72.3 and 96.9, respectively. Compared to the TX at the same dose (10 mg/kg), the VES stabilized emulsion formulation was equally efficacious based on RTV, T/C and percentage of tumor inhibition, but this VES stabilized emulsion formulation appeared less toxic than TX based on body weight. Compared to the TX additional tumor reduction was observed with VES stabilized emulsion formulation 20 mg/kg based on RTV and T/C.

CONCLUSION: The VES stabilized emulsion formulation exhibited significant anticancer activity, in a dose dependent fashion, against xenografted MDAMB-435 human breast cancer in nude mice (Balb/c). This VES stabilized emulsion formulation is at least as efficacious as the TAXOTERE™ formulation.

Example 11

A Study of Vein Irritation at Injection Site for a VES-Stabilized Emulsion Formulation of Docetaxel According to this Invention AIM: To evaluate the vein irritation potential of a VES-stabilized emulsion formulation of docetaxel according to Example 1 and to demonstrate local safety at the injection site.

METHODS: Using the standard rabbit marginal ear vein model, the VES stabilized emulsion formulation was infused at the maximum clinical docetaxel infusion concentration (0.06 mg/mL) at a rate of 1.0 mL/min with 30 mL per rabbit. Injections were given once a day for three consecutive days. The control group was infused with a 5% dextrose solution for injection (D5W).

RESULTS: During the infusion, the animals were quiet with steady breath. After each infusion, no edema or redness was observed at the injection site. Forty-eight hours after the last infusion, animals were sacrificed and the marginal ear vein with surrounding tissue from the down stream section of the injection site was removed for histopathological examination. No tissue inflammation, denaturation, necrosis or other signs of irritation was observed.

CONCLUSION: The VES stabilized emulsion formulation did not cause vein irritation and meets the requirement for injection site safety.

Example 12

Investigation of Hemolytic Potential of a Novel Docetaxel Emulsion

AIM: To determine the hemolytic potential of a VES-stabilized emulsion formulation of docetaxel according to Example 1. Polysorbate 80 is reported to be the allergenic component in the currently marketed docetaxel formulation (TAXOTERE™).

METHODS: Visual examination of hemolysis or aggregation, in vitro, in 2% rabbit red blood cells (RBC) suspended in a normal saline solution containing the VES stabilized emulsion formulation according to Example 1. The VES stabilized emulsion formulation was adjusted to a concentration used clinically and mixed with a 2% rabbit RBC suspension at various ratios; the mixtures were incubated at 37° C. for 3 hours and observed for hemolysis and aggregation.

RESULTS: No hemolysis or aggregation was observed at any mixing ratio.

CONCLUSION: The VES stabilized emulsion formulation is non-hemolytic.

Example 13

A VES-stabilized suspension formulation of paclitaxel (Table 1.4) was prepared as in a composition as described below.

TABLE 1.4

| Component | % w/w |
| --- | --- |
| Paclitaxel | 0.5 |
| Egg lecithin, USP/EP | 8.8 |
| Cholesterol, NF | 1.2 |
| Vitamin E Succinate, USP | 3.6 |
| Sucrose, NF | 17.5 |
| De-ionized water, qs to | 100 |

The VES-stabilized suspension formulation of paclitaxel was prepared by the double-homogenization technique similar to that in EXAMPLE 1. The average particle was less than 200 nm and the suspension was sufficiently stable to be freeze-dried. Without VES, a stable suspension was not obtainable according to this composition and method of preparation.

Example 14

Another VES-stabilized emulsion formulation of docetaxel (Table 1.5) is prepared as in a composition as described below.

TABLE 1.5

| Component | % w/w |
| --- | --- |
| Docetaxel | 0.1-1.0 |
| Medium chain triglyceride, EP | 4 |
| Soybean Oil, USP | 4 |
| Lecithin, USP/EP | 10 |
| Cholesterol, NF | 0.6 |
| Vitamin E Succinate, USP | 0.3 |
| Dextrose, USP/NF | 17.5 |
| De-ionized water, qs to | 100 |

The VES-stabilized emulsion formulation of docetaxel is prepared by the double-homogenization technique as described in EXAMPLE 1.

Example 15

A VES-stabilized suspension formulation of docetaxel (Table 1.6) is prepared as in a composition as described below.

TABLE 1.6

| Component | % w/w |
| --- | --- |
| Docetaxel | 0.5 |
| Lecithin, USP/EP | 8.8 |
| Cholesterol, NF | 1.2 |
| Vitamin E Succinate, USP | 3.6 |
| Sucrose, NF | 17.5 |
| De-ionized water, qs to | 100 |

The VES-stabilized suspension formulation of docetaxel is prepared by the double-homogenization technique similar to that in EXAMPLE 1.

Example 16

A VES-stabilized emulsion formulation of paclitaxel (Table 1.7) is prepared as in a composition as described below.

TABLE 1.7

| Component | % w/w |
| --- | --- |
| Paclitaxel | 0.1-1.0 |
| Medium chain triglyceride, EP | 4 |
| Soybean Oil, USP | 4 |
| Lecithin, USP/EP | 10 |
| Cholesterol, NF | 0.6 |
| Vitamin E Succinate, USP | 0.3 |
| Dextrose, NF | 17.5 |
| De-ionized water, qs to | 100 |

The VES-stabilized emulsion formulation of paclitaxel is prepared by the double-homogenization technique as described in EXAMPLE 1.

Example 17

A VES-stabilized emulsion formulation of itraconazole (Table 1.8) is prepared as in a composition as described below.

TABLE 1.8

| Component | % w/w |
| --- | --- |
| Itraconazole | 0.1-1.0 |
| Medium chain triglyceride, EP | 4 |
| Soybean Oil, USP | 4 |
| Lecithin, USP/EP | 10 |
| Cholesterol, NF | 0.6 |
| Vitamin E Succinate, USP | 0.3 |
| Sucrose, NF | 17.5 |
| De-ionized water, qs to | 100 |

The VES-stabilized emulsion formulation of itraconazole is prepared by the double-homogenization technique as described in EXAMPLE 1.

Example 18

A VES-stabilized emulsion formulation of amphotericin B (Table 1.9) is prepared as in a composition as described below.

TABLE 1.9

| Component | % w/w |
| --- | --- |
| Amphotericin B | 0.1-1.0 |
| Medium chain triglyceride, EP | 4 |
| Soybean Oil, USP | 4 |
| Lecithin, USP/EP | 10 |
| Cholesterol, NF | 0.6 |
| Vitamin E Succinate, USP | 0.3 |
| Sucrose, NF | 17.5 |
| De-ionized water, qs to | 100 |

The VES-stabilized emulsion formulation of amphotericin B is prepared by the double-homogenization technique as described in EXAMPLE 1.

Example 19

A VES-stabilized emulsion formulation of vericonazole (Table 1.10) is prepared as in a composition as described below.

TABLE 1.10

| Component | % w/w |
| --- | --- |
| Vericonazole | 0.1-1.0 |
| Medium chain triglyceride, EP | 4 |
| Soybean Oil, USP | 4 |
| Lecithin, USP/EP | 10 |
| Cholesterol, NF | 0.6 |
| Vitamin E Succinate, USP | 0.3 |
| Dextrose, NF | 17.5 |
| De-ionized water, qs to | 100 |

The VES-stabilized emulsion formulation of vericonazole is prepared by the double-homogenization technique as described in EXAMPLE 1.

Example 20

A VES-stabilized emulsion formulation of paclitaxel (Table 1.11) was prepared as in a composition as described below.

TABLE 1.11

| Component | % w/w |
| --- | --- |
| Paclitaxel, USP | 0.4 |
| Medium chain triglyceride, EP | 4 |
| Soybean Oil, USP | 4 |
| Soy Lecithin, USP/EP | 10 |
| Cholesterol, NF | 0.6 |
| Vitamin E Succinate, USP | 0.3 |
| Sucrose, NF | 1.75 |
| Dextrose Low endotoxin | 15.75 |
| De-ionized water, qs to | 100 |

The VES-stabilized emulsion formulation of paclitaxel was prepared by the double-homogenization technique as described in EXAMPLE 1.

Studies were conducted to evaluate the stability of paclitaxel (chemical stability) in the VES-stabilized emulsion and the stability of the emulsion itself (physical stability) according to Example 5. The chemical stability was determined based on concentration and purity of paclitaxel in the emulsion over time. The paclitaxel concentration and purity in the emulsion were determined by a reversed phase high-pressure liquid chromatography (Hewlett Packard Model 1050 HPLC). The physical stability was evaluated based on the average oily droplet diameter. The average oil droplet diameter was measured using a laser light scattering spectrometer (Model ZEN3600, Zetasizer, Nano series by Malvern). The results are shown in the tables below.

| Storage Condition | Paclitaxel Concentration (mg/mL) by HPLC | |
| --- | --- | --- |
|  | Initial | 1 month |
| −20° C. | 3.7 | 4.42 |
| 5° C. |  | 3.89 |
| 25° C. |  | 3.83 |
| 30° C. |  | 3.86 |

| Storage Condition | Average Droplet Diameter by Laser Light Scattering Measurement (nm) | |
|---|---|---|
| | Initial | 1 month |
| −20° C. | 93.9 | 94.9 |
| 5° C. | | 104 |
| 25° C. | | 126 |
| 30° C. | | 189 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A vitamin E succinate (VES) stabilized oil-in-water emulsion comprising: vitamin E succinate (VES) and
oil droplets in an aqueous medium, wherein the oil droplets comprise a substantial portion of a substantially water insoluble pharmacologically active agent, wherein the pharmacologically active agent in the emulsion consists of docetaxel; wherein
the average diameter of the droplets being no greater than about 1 micron, wherein the emulsion is stabilized by a submicron suspension of vitamin E succinate (VES), and the emulsion has a zeta potential between −20 mV and −50 mV.

2. The emulsion according to claim 1, wherein the emulsion is sterilized by filtration.

3. The emulsion according to claim 1, wherein the oil droplets of the emulsion are liquid or are free of crystalline solid at ambient temperature, and wherein the pharmacologically active agent is substantially dissolved in the oil droplets.

4. The emulsion according to claim 1, prepared by a double homogenization method, comprising:
 a. homogenizing VES in water to form a submicron VES suspension;
 b. dissolving the substantially water insoluble pharmacologically active agent in an oil solution containing at least one injectable oil and at least one injectable phospholipid to form an oil phase;
 c. combining the submicron VES suspension, the oil phase and optionally other pharmaceutically acceptable ingredients to form a mixture; and
 d. homogenizing the mixture to produce the emulsion.

5. The emulsion of claim 1, comprising at least one injectable oil, injectable phospholipids and water, wherein the average diameter of the oil droplets is less than 200 nm, and the docetaxel-to-oil ratio is no less than 1:50 by weight.

6. The emulsion according to claim 1, wherein
a. docetaxel is in a weight percentage concentration range of 0.1 to 1;
b. vitamin E succinate is in a weight percentage concentration range of 0.1 to 3;
c. the at least one injectable oil is a vegetable oil in a weight percentage concentration range of 1 to 10;
d. optionally, a medium chain triglyceride oil is in a weight percentage concentration range of 1 to 10;
e. a phospholipid is in a weight percentage concentration range of 1 to 20;
f. optionally, cholesterol is in a weight percentage concentration range of 0.01 to 5;
g. water is in a weight percentage concentration range of 40 to 90; and
h. the pH of the emulsion is about 5 to 9.

7. The emulsion according to claim 6, further comprising a bulking agent selected from dextrose, sucrose, lactose and a mixture thereof in a weight percentage concentration range of 5 to 50.

8. A suspension, said suspension comprising: vitamin E succinate (VES) and
submicron solid particles of an amorphous or crystalline pharmacologically active agent, wherein the pharmacologically active agent in the suspension consists of docetaxel; wherein
the pharmacologically active agent is dispersed in an aqueous medium and stabilized by VES, wherein the solid particles are substantially free of liquid oil, have an average diameter of less than 200 nm and a zeta potential between −20 mV and −50 mV.

9. The suspension according to claim 8, wherein the suspension comprises:
docetaxel in a weight percentage concentration range of about 0.1 to about 1.0;
lecithin in a weight percentage concentration range of about 5 to about 15;
cholesterol in a weight percentage concentration range of about 0.5 to about 2;
VES in a weight percentage concentration range of about 0.1 to about 5;
a bulking agent selected from sucrose, dextrose, lactose, and a mixture thereof in a weight percentage concentration range of about 10 to about 20; and water.

10. The emulsion according to claim 1, wherein the oil droplets comprise no less than about 70% of the substantially water insoluble pharmacologically active agent.

11. The emulsion according to claim 1, wherein the emulsion comprises VES in a weight percentage concentration range of 0.1 to 1.2.

12. The emulsion according to claim 1, comprising
a. docetaxel in a weight percentage concentration range of 0.1 to 1;
b. VES in a weight percentage concentration range of 0.2 to 1;
c. a vegetable oil in a weight percentage concentration range of 3 to 5;
d. a medium chain triglyceride oil in a weight percentage concentration range of 3 to 5;
e. a phospholipid in a weight percentage concentration range of 8 to 12;
f. cholesterol in a weight percentage concentration range of 0.4 to 0.8; and
g. water.

13. The emulsion according to claim 1, wherein the docetaxel is docetaxel trihydrate.

14. The suspension according to claim 8, wherein the docetaxel is docetaxel trihydrate.

15. The emulsion according to claim 1, wherein:
a. docetaxel in a weight percentage concentration range of 0.1 to 1;
b. vitamin E succinate in a weight percentage concentration range of 0.1 to 3;
c. a vegetable oil in a weight percentage concentration range of 1 to 10;

d. a medium chain triglyceride oil in a weight percentage concentration range of 1 to 10;

e. a phospholipid in a weight percentage concentration range of 1 to 20;

f. cholesterol in a weight percentage concentration range of 0.01 to 5; and g. water.

16. The stabilized emulsion according to claim 15, further comprising a bulking agent selected from the group consisting of dextrose, sucrose, lactose and a mixture thereof in a weight percentage concentration range of 5 to 50.

17. The stabilized emulsion according to claim 15, wherein the docetaxel is in a weight percentage of 0.6.

18. The stabilized emulsion according to claim 15, wherein the VES is in a weight percentage concentration range of 0.2 to 1.

19. The stabilized emulsion according to claim 15, wherein the vegetable oil is in a weight percentage concentration range of 3 to 5.

20. The stabilized emulsion according to claim 15, wherein the medium chain triglyceride oil is in a weight percentage concentration range of 3 to 5.

21. The stabilized emulsion according to claim 15, wherein the phospholipid is a weight percentage concentration range of 8 to 12.

22. The stabilized emulsion according to claim 15, wherein cholesterol in a weight percentage concentration range of 0.4 to 0.8.

23. The stabilized emulsion according to claim 15, wherein the docetaxel is docetaxel trihydrate.

24. The emulsion according to claim 1, wherein:

a. docetaxel in a weight percentage concentration range of 0.1 to 1;

b. VES in a weight percentage concentration range of 0.2 to 1;

c. a vegetable oil in a weight percentage concentration range of 3 to 5;

d. a medium chain triglyceride oil in a weight percentage concentration range of 3 to 5;

e. a phospholipid in a weight percentage concentration range of 8 to 12;

f. cholesterol in a weight percentage concentration range of 0.4 to 0.8; and g. water.

25. The stabilized oil-in-water emulsion according to claim 24, wherein the docetaxel is docetaxel trihydrate.

26. The emulsion according to claim 1, wherein:

a. docetaxel in a weight percentage of 0.6;

b. vitamin E succinate in a weight percentage of 0.3;

c. a soybean oil in a weight percentage of 4;

d. a medium chain triglyceride oil in a weight percentage 4;

e. a phospholipid in a weight percentage of 10;

f. cholesterol in a weight percentage of 0.6; and g. water.

27. The stabilized oil-in-water emulsion according to claim 26, wherein the docetaxel is docetaxel trihydrate.

* * * * *